(12) United States Patent
Charkhgard et al.

(10) Patent No.: US 12,059,578 B2
(45) Date of Patent: Aug. 13, 2024

(54) FLUENCY MAP OPTIMIZATION IN INTENSITY-MODULATED RADIATION THERAPY

(71) Applicant: University of South Florida, Tampa, FL (US)

(72) Inventors: Hadi Charkhgard, Tampa, FL (US); Payman Ghasemi Saghand, Lutz, FL (US)

(73) Assignee: UNIVERSITY OF SOUTH FLORIDA, Tampa, FL (US)

(*) Notice: Subject to any disclaimer, the term of this patent is extended or adjusted under 35 U.S.C. 154(b) by 408 days.

(21) Appl. No.: 17/559,912

(22) Filed: Dec. 22, 2021

(65) Prior Publication Data
US 2022/0193449 A1 Jun. 23, 2022

Related U.S. Application Data

(60) Provisional application No. 63/199,370, filed on Dec. 22, 2020.

(51) Int. Cl.
*A61N 5/10* (2006.01)
*G06T 7/00* (2017.01)
(Continued)

(52) U.S. Cl.
CPC ......... *A61N 5/1039* (2013.01); *A61N 5/1031* (2013.01); *A61N 5/1045* (2013.01);
(Continued)

(58) Field of Classification Search
CPC .. A61N 5/1039; A61N 5/1031; A61N 5/1045; G06T 7/0012; G06T 7/60;
(Continued)

(56) References Cited

U.S. PATENT DOCUMENTS 11,191,423 B1* 12/2021 Zingaretti ............... G06T 19/00
2004/0165696 A1* 8/2004 Lee ....................... G16H 20/40
378/65

(Continued)

OTHER PUBLICATIONS

Breedveld et al., "The equivalence of multi-criteria methods for radiotherapy plan optimization," Nov. 17, 2009, pp. 7199-7209 (12 pages), Phys. Med. Biol. 54, Institute of Physics and Engineering in Medicine, IOP Publishing.

(Continued)

*Primary Examiner* — Md K Talukder
(74) *Attorney, Agent, or Firm* — Quarles & Brady LLP

(57) ABSTRACT

A method for controlled tumoricidal radiation dose delivery is disclosed. The method includes obtaining an image of a body organ; diving the image into a plurality of voxels; determining a set of feasible actions for the body organ by identifying an upper bound and a lower bound for the body organ; determining a utility function for the body organ; determining a disagreement point by identifying an ideal fluency map and a worst fluency map; determining a negotiation power weight based on a type of the body organ; and optimizing the plurality of radiation dose levels to the plurality of voxels based on the set of feasible actions, the utility function, the disagreement point, and the negotiation power weight. Other aspects, embodiments, and features are also claimed and described.

26 Claims, 10 Drawing Sheets

(51) Int. Cl.
  *G06T 7/60* (2017.01)
  *G06T 11/00* (2006.01)
  *G16H 20/40* (2018.01)
  *G16H 30/40* (2018.01)

(52) U.S. Cl.
  CPC .............. *G06T 7/0012* (2013.01); *G06T 7/60* (2013.01); *G06T 11/008* (2013.01); *G16H 20/40* (2018.01); *G16H 30/40* (2018.01); *G06T 2207/10081* (2013.01); *G06T 2207/30096* (2013.01)

(58) Field of Classification Search
  CPC ......... G06T 11/008; G06T 2207/10081; G06T 2207/30096; G16H 20/40; G16H 30/40; G16H 10/60
  See application file for complete search history.

(56) References Cited

U.S. PATENT DOCUMENTS

| | | | | |
|---|---|---|---|---|
| 2013/0217948 A1* | 8/2013 | Mihaylov | ............ | A61N 5/1031 600/1 |
| 2022/0008748 A1* | 1/2022 | Huang | ................ | A61N 5/1077 |
| 2022/0193449 A1* | 6/2022 | Charkhgard | ......... | A61N 5/1039 |
| 2023/0196515 A1* | 6/2023 | Koch | .................... | G06T 3/4046 382/128 |
| 2023/0264045 A1* | 8/2023 | Sjolund | ................ | A61N 5/1031 600/1 |
| 2023/0302298 A1* | 9/2023 | Bengtsson | ........... | A61N 5/1031 |

OTHER PUBLICATIONS

Charkhgard et al., "The Magic of Nash Social Welfare in Optimization: Do Not Sum, Just Multiply!" Mar. 2020, pp. 1-18 (19 pages).

Craft et al., "Shared data for intensity modulated radiation therapy (IMRT) optimization research: the CORT dataset," Dec. 12, 2014, 12 pages, GigaScience.

Long et al., "Threshold-driven optimization for reference-based auto-planning," Feb. 7, 2018, pp. 1-7 (8 pages), Phys. Med. Biol. 63 04NT01, Institute of Physics and Engineering in Medicine, IOP Publishing.

Saghand et al., "A Branch-and-Bound Algorithm for a Class of Mixed Integer Linear Maximum Multiplicative Programs: A Bi-objective Optimization Approach," Aug. 6, 2018, pp. 263-274 (12 pages), vol. 101, Jan. 2019, Computers & Operations Research.

* cited by examiner

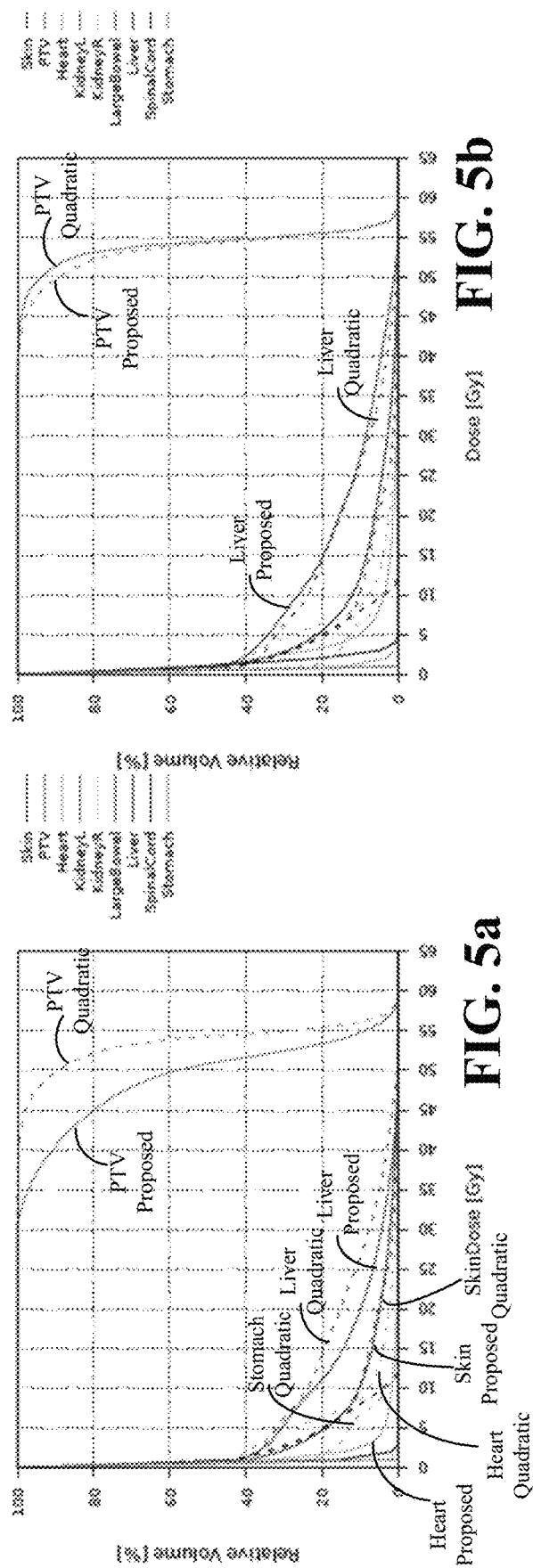
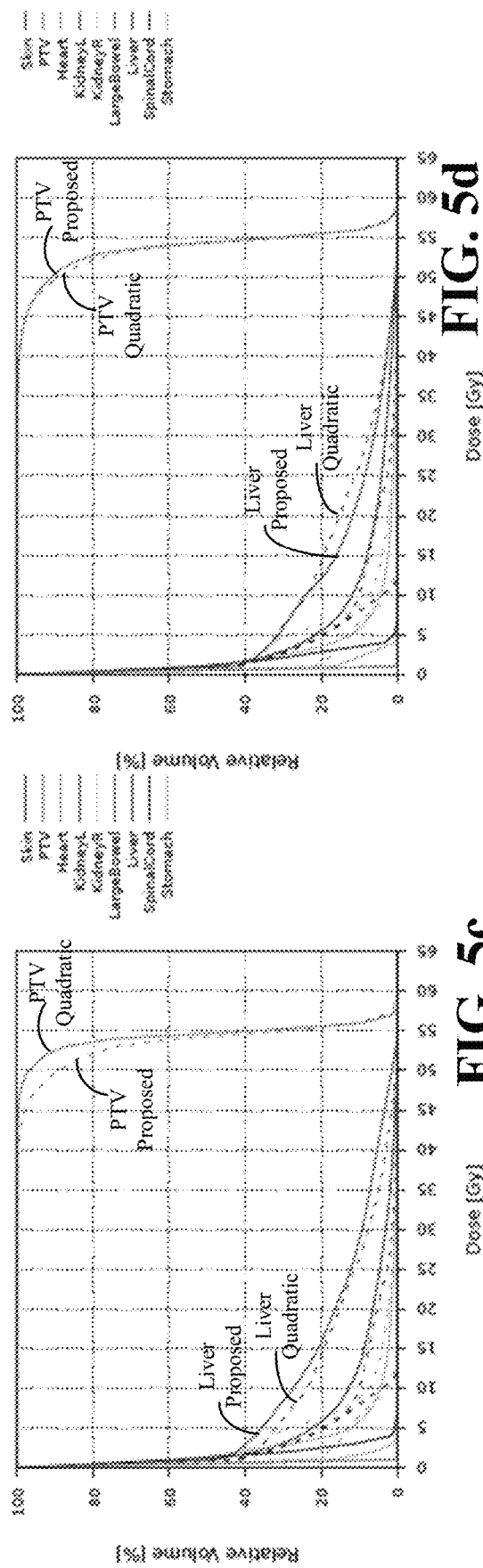
FIG. 5a
FIG. 5b
FIG. 5c
FIG. 5d

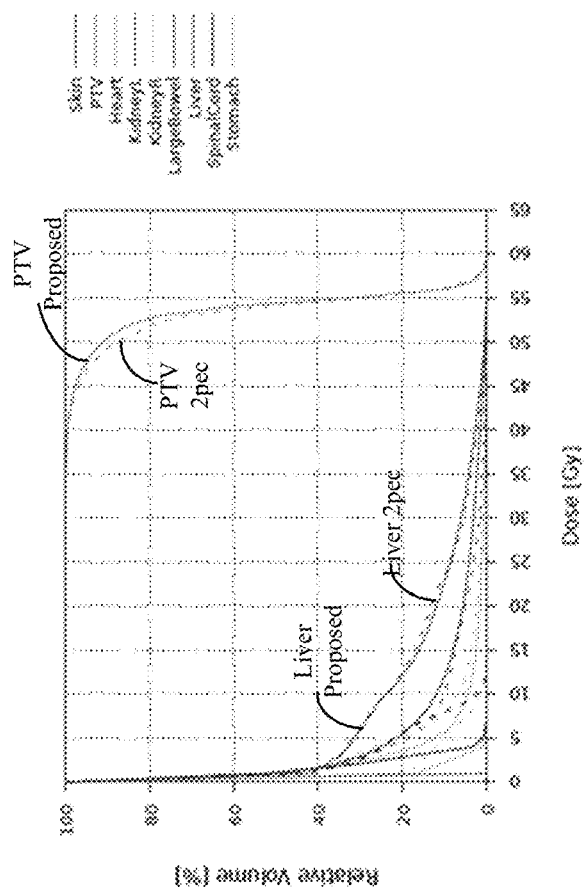
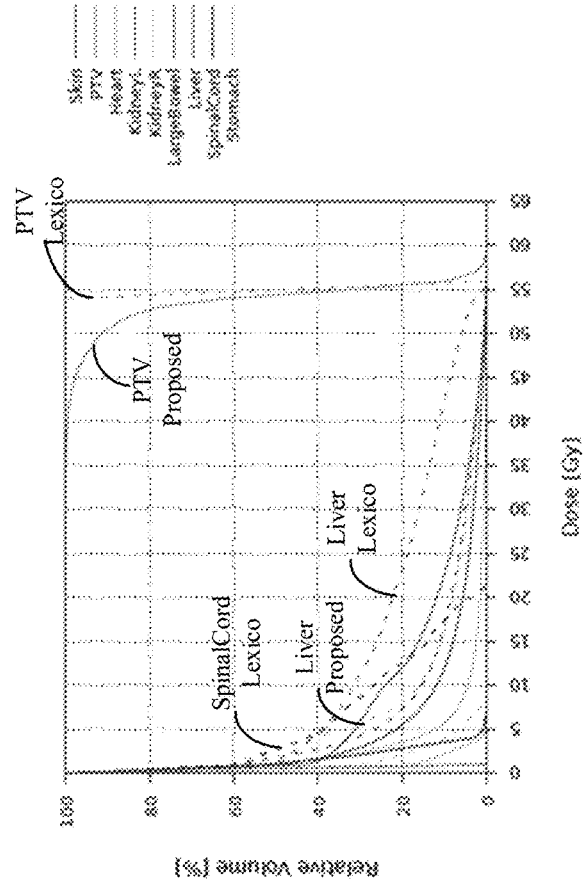
FIG. 7b
FIG. 7a

FLUENCY MAP OPTIMIZATION IN INTENSITY-MODULATED RADIATION THERAPY

CROSS-REFERENCE TO RELATED CASES

The present disclosure claims priority to U.S. Provisional Application No. 63/199,370, filed on Dec. 22, 2020, the content of which application is hereby incorporated by reference in its entirety.

STATEMENT OF GOVERNMENT SUPPORT

N/A

TECHNICAL FIELD

The technology discussed below relates generally to fluency map optimization, and more particularly, to fluency map optimization using a cooperative game solution approach.

BACKGROUND

Cancerous tissues are fast proliferating cells that are more sensitive to radiation compared to healthy cells. This fact provides the basis to fight against cancers using radiotherapy. In radiotherapy, radiation doses are delivered to cancerous cells which helps shrink or eliminate the tumors. One of the radiotherapy methods is Intensity Modulated Radiation Therapy (IMRT) that uses computer-controlled accelerators to deliver radiation doses to a tumor or specific areas within the tumor. IMRT controls the intensity of the radiation beam in multiple small volumes and helps the radiation dose to conform to the 3D shape of the target area. In IMRT, planning is a critical problem which concerns with the choice of the best setting of radiation. In IMRT planning, the goal is to select the emission plan that assures the deliverance of tumoricidal radiation doses to Planning Target Volume (PTV) with the minimal impact on healthy organs, referred to as Organs At Risk (OAR). However, it is very difficult to find a desirable balance the trade-offs between sacrificing some OAR's or sparing some PTV's. What are needed are systems and methods that address one or more of these shortcomings.

SUMMARY

The following presents a simplified summary of one or more aspects of the present disclosure, in order to provide a basic understanding of such aspects. This summary is not an extensive overview of all contemplated features of the disclosure, and is intended neither to identify key or critical elements of all aspects of the disclosure nor to delineate the scope of any or all aspects of the disclosure. Its sole purpose is to present some concepts of one or more aspects of the disclosure in a simplified form as a prelude to the more detailed description that is presented later.

In one example, a method, a system, and/or an apparatus for is disclosed. The method, the system implementing the method, and/or the apparatus implementing the method may include obtaining an image of a body organ; diving the image into a plurality of voxels; determining a set of feasible actions for the body organ by identifying an upper bound and a lower bound for the body organ; determining a utility function for the body organ; determining a disagreement point by identifying an ideal fluency map and a worst fluency map; determining a negotiation power weight based on a type of the body organ; and optimizing the plurality of radiation dose levels to the plurality of voxels based on the set of feasible actions, the utility function, the disagreement point, and the negotiation power weight.

These and other aspects of the invention will become more fully understood upon a review of the detailed description, which follows. Other aspects, features, and embodiments of the present invention will become apparent to those of ordinary skill in the art, upon reviewing the following description of specific, exemplary embodiments of the present invention in conjunction with the accompanying figures. While features of the present invention may be discussed relative to certain embodiments and figures below, all embodiments of the present invention can include one or more of the advantageous features discussed herein. In other words, while one or more embodiments may be discussed as having certain advantageous features, one or more of such features may also be used in accordance with the various embodiments of the invention discussed herein. In similar fashion, while exemplary embodiments may be discussed below as device, system, or method embodiments it should be understood that such exemplary embodiments can be implemented in various devices, systems, and methods.

BRIEF DESCRIPTION OF THE DRAWINGS

FIGS. 5a-5d are an illustration of an example of liver case: DVH comparison between the Nash optimal solution and the quadratic optimal solution according to some embodiments.

FIGS. 7a-7b are an illustration of an example of liver case: DVH comparison between the Nash optimal solution and Lexicographic optimization or 2pεc approach according to some embodiments.

DETAILED DESCRIPTION

Figure 1C:
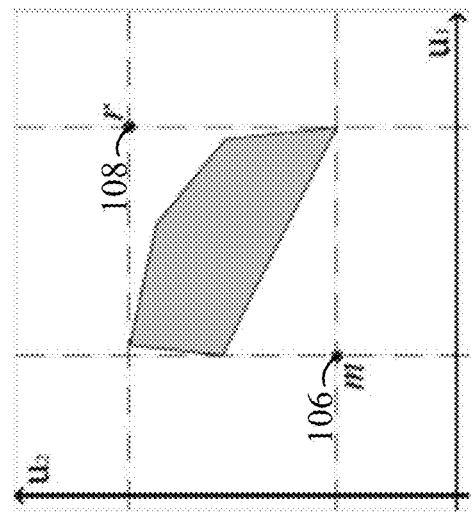
FIGS. 1a-1c are an illustration of an example of the feasible set of a bargaining game with two player ($|S|=2$) in the payoff space according to some embodiments.

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known structures and components are shown in block diagram form in order to avoid obscuring such concepts.

1. SUMMARY

This present disclosure discusses the fluency map optimization problem in Intensity Modulated Radiation Therapy (IMRT) from a cooperative game theory point of view. The disclosure considers the cancerous and healthy organs in a patient's body as players of a game, where cancerous organs seek to eliminate the cancerous cells and healthy organs seek to receive no harm. The goal is to balance the trade-offs between the utility of players by forming a grand coalition between them. For the goal, the disclosure discusses a methodology that solves a few convex optimization problems in order to transform the fluency map optimization problem into a bargaining game. To solve the bargaining game, the concept of Nash Social Welfare (NSW) optimization is employed due to the desirable efficiency and fairness properties of its outcomes. The proposed NSW optimization is convex and can be solved by powerful commercial optimization software. An additional advantage of the proposed approach is that it has a new control lever for the fluency map optimization, the so-called negotiation powers, which enables practitioners to put more emphasis on an organ by changing its negotiation power. To show the efficacy of the discussed methodology, the methodology is applied to the TG-119 case and a liver case. The proposed approach is compared with a state-of-the-art approach through creating Dose Volume Histograms.

2. INTRODUCTION

Cancerous tissues are fast proliferating cells that are more sensitive to radiation compared to healthy cells. This fact provides the basis to fight against cancers using radiotherapy. In radiotherapy, radiation doses are delivered to cancerous cells which helps shrink or eliminate the tumors. One of the radiotherapy methods is Intensity Modulated Radiation Therapy (IMRT) that uses computer-controlled accelerators to deliver radiation doses to a tumor or specific areas within the tumor. IMRT controls the intensity of the radiation beam in multiple small volumes and helps the radiation dose to conform to the 3D shape of the target area. In IMRT, planning is a critical problem which concerns with the choice of the best setting of radiation. In IMRT planning, the goal is to select the emission plan that assures the deliverance of tumoricidal radiation doses to Planning Target Volume (PTV) with the minimal impact on healthy organs, referred to as Organs At Risk (OAR). The planning is usually divided into three phases, namely: i) the selection of the radiation angles and beams (beam angle optimization), ii) the design of fluency map or intensity pattern (fluency map optimization), iii) the design of a delivery sequence (segmentation problem).

This disclosure discusses the second step, i.e., fluency map optimization. One motivation is that, although the entire process of fluency map optimization is based on the trade-offs between killing cancerous cells and not harming healthy cells, modeling these trade-offs from the angle of cooperative game theory does not exist. Therefore, the disclosure uses a game theoretical approach to create a cooperative game by focusing on modeling the trade-offs occurring in the fluency map optimization problem. To do so, in this section, the disclosure provides a brief explanation of how a fluency map optimization is mathematically modeled. Then, the motivation and a brief explanation of the contributions follows. Finally, the disclosure provides the main structure.

In fluency map optimization, the assumption is that a number of beam angles are provided, and the problem is to design a fluency map which maximizes the dose delivered to PTV while minimizing the doses deposited in OAR. To calculate the depositions made by the radiations of the selected beam angles, the 3D computed tomography (CT) of the patient may be used. The patient's body can be considered as a net of small volume elements, referred to as Voxels, and the dose deposition can be modeled to show how much the amount of depositions in different body voxels will be if a specific beam or a group of beams radiate.

The dose deposition model is non-linear in nature; however, the linear dose deposition matrices can provide adequately precise approximations of the depositions. This, in specific, is of benefit as it enables modeling the constraints of the fluency map optimization using linear functions rather than non-linear relations. To present the linear deposition relations, the set of all beamlets can be denoted by N and the set of all body voxels by V. Further, the vector of variables can be defined as $x := (x_1, \ldots, x_{|N|})$, where $x_n$ represents the amount of radiation of beamlet $n \in N$, and $D_{vn}$ can be defined as the amount of deposition in voxel $v \in V$ if beamlet n emits one unit radiation, i.e., $x_n = 1$. Also, the vector of doses can be defined as $d := (d_1, \ldots, d_{|V|})$, where $d_v$ is the amount of the total doses deposited in voxel $v \in V$. With these definitions, the set of all possible fluency maps can be written as:

$$\mathcal{D} := \{d \in \mathbb{R}_+^{|V|} : d_v = \Sigma_{n \in N} D_{vn} x_n \, \forall v \in V, x \geq 0\}. \quad \text{Equation 1}$$

Having defined the deposition relations, a dose prescription may be used to design the fluency map based on it. The dose prescription typically includes a lower and upper dose level for each organ or voxel in the body. A common problem with the clinical dose prescriptions is that designing the ideal fluency map delivering such prescriptions is almost impossible. This is due to the fact that delivering the tumoricidal radiation doses to PTV often requires the violation of some of the prescribed bounds for healthy voxels. Therefore, instead of finding a plan satisfying the prescription, the fluency map optimization problem can be stated as finding a plan that minimizes the deviations from the prescribed levels. That said, the fluency map optimization problem can be stated as:

$$\min_{d \in \mathcal{D}} f(d). \quad \text{Equation 2}$$

In Equation 2, $f(d)$ represents the non-negative function that measures the deviations, which can be linear, quadratic, or (convex) non-linear in general. In the disclosure, quadratic penalty functions are discussed. However, it should be appreciated that the proposed approach is generic and can be customized for any other forms.

To define the quadratic penalty function, the dose prescription by (l, u) can be shown. Also, $l := (l_1, \ldots, l_{|V|})$ and $u := (u_1, \ldots, u_{|V|})$ can be defined as the respective vector of lower and upper lose levels such that $l_v$ and $u_v$ show the lower and upper dose levels prescribed for voxel $v \in V$. In addition, $\alpha:=(\alpha_1, \ldots, 1_{|V|})$ can be defined as the vector of non-negative real numbers where $\alpha_v$ represents the importance of voxel $v \in V$. Using these notations/definitions, the quadratic fluency map optimization problem can be defined as $$\min_{d \in \mathcal{D}} f(d) = \sum_{v \in V} \alpha_v [(d_v - u_v)_+^2 + (l_v - d_v)_+^2]. \quad \text{Equation 3}$$

In Equation 3, $(Y)_+ := \max(0, Y)$. Observe that Equation 3 penalizes the doses that surpass the upper bound or fall below the lower bound by emphasizing the higher deviations.

Ideally, the (l, u) is defined as $$l_v = u_v = \begin{cases} 0, & \text{when } v \text{ is } OAR, \\ T_v, & \text{when } v \text{ is } PTV \end{cases} \quad \text{Equation 4}$$

In Equation 4, $T_v$ is the dose level required to eliminate the PTV. Such prescription often makes the optimal objective value of Equation 3 non-zero. Such a non-zero value does not provide any information other than implying that it is impossible to not violate the prescribed dose levels. This lack of interpretability in the objective values constructs the main weakness of quadratic penalty functions. Specifically, due to this weakness, the plans cannot be simply evaluated using their penalty functions' values. As a result, the fluency map plans are usually evaluated and compared using their Dose Volume Histogram (DVH), a histogram relating radiation dose to tissue volume. By means of clarity, a DVH is a 2D plot where the vertical axis represents the percentage volume and the horizontal axis shows the dose amount. Then, the height of a point on the plot provides the percentage volume of the structure that receives a dose greater than or equal to the length of that point.

The second weakness of quadratic penalty functions is that they do not suffice to create a plan with a clinically acceptable DVH, and the burden is on the manipulation of the importance weights, i.e., $\alpha$, to adjust the DVH of the final plan. Their third weakness is that the importance weights have no clinical meaning and are priorly unknown, their choice is quite arbitrary, and they are patient-specific. Therefore, several plans with different choice of weights have to be tried before selecting a final plan. All of these add to the complexity of the problem in terms of both time and computation.

To handle the problem of importance weights, an automated framework that iteratively updates the weights in voxel level can be used, but some issues regarding the consistency in quality and control on the trade-offs may exist. Moreover, if the initial dose prescription is feasible, then the objective value of Equation 3 will be zero making the importance weights completely useless in improving the DVH of the final plan. Therefore, instead of weights, the prescribed dose levels can be used as the driving force. A threshold-driven penalty function can be used, where they updated the thresholds iteratively to attain a desired plan. However, the approach is more of a re-planning or adaptive planning rather than a blank-start optimizer for IMRT. In addition, in their proposed approach, they add some quadratic terms to the original quadratic penalty function which escalates the problem of meaningless penalty values and importance weights.

This disclosure addresses these issues by employing the concept of bargaining from the field of cooperative game theory. This disclosure finds a solution that can desirably balance the trade-offs between sacrificing some OAR's or sparing some PTV's from a bargaining point of view.

In order to discuss the examples of this disclosure, a brief definition of the bargaining game in the field of game theory is provided. The bargaining problem is a game where all (competing) players agree to create a grand coalition, instead of competing with each other, to get higher payoffs. To be able to create a grand coalition, the agreement of all players is necessary. Therefore, the main concern when dealing with a bargaining problem is what the payoff of each player should be in a grand coalition (and how it should be computed). One of the solution techniques for this problem can use a super-criterion that will be optimized over the feasible allocation of payoffs. This supercriterion is known as the Nash Social Welfare (NSW) function and it guarantees both efficiency and fairness in the solution that it obtains.

One example of this disclosure is to transform the fluency map optimization problem into a bargaining problem. This transformation is performed in organ level where different body organs are considered as different players with different negotiation powers. As an overview, our approach takes a dose prescription and a penalty function for each organ as inputs and then constructs a bargaining game between them and finds a solution for it. To be able to construct the bargaining problem, 2|S|+1 optimization problems can be solved, where S represents the set of body organs (under consideration). Having constructed the bargaining problem, its corresponding optimization problem will be solved to find the desirable fluency map, which will be a Nash optimal solution. Overall, the exemplary methodology in the disclosure has several advantages and resolves the weaknesses of the state-of-the-art techniques as explained below.

First, the exemplary methodology provides the practitioners with the flexibility of using any form of penalty functions as their inputs. However, as mentioned earlier, quadratic penalty functions are used in the methodology.

Second, given the convexity of input penalty functions, all optimization problems in the methodology are convex and can be solved to optimality in polynomial times.

Third, the methodology resolves the weakness of interpretability as the penalty functions can be transformed to preference functions. Considering that the new objective values are now meaningful, the different plans can be easily evaluated and compared with respect to their objective values.

Fourth, a new control lever is introduced in an exemplary modeling referred to as negotiation powers. These powers provide the practitioners with the flexibility of putting more emphasis on an organ by changing its negotiation power.

Finally, although the methodology focuses on the trade-offs in organ level and uses the negotiation powers as a lever of controlling the trade-offs, voxel weights and organ weights can be included in the disclosed model to provide the ability to control the trade-offs in all levels.

The remainder of this disclosure is organized as follows. Section 3 provides the preliminaries of bargaining problems and how these problems can be optimized. Section 4 provides the details of our methodology by explaining each step in the process of transforming a fluency map optimization to a bargaining problem. Section 5 provides a theoretical discussion about the proposed approach from the angle of multi-criteria optimization. Section 6 provides some numerical results by implementing our approach on some instances available in the literature and generating some different plans. Finally, Section 7 concludes the disclosure.

3. PRELIMINARIES

In this section, we will discuss the preliminaries of bargaining games. In general, to create a bargaining game, four pieces of information are required:

First, the set of feasible actions available for each player: before starting bargaining, players will assess their set of actions and will join the game when they are fully aware of the actions that are feasible for them to take.

Second, the utility function of each player: based on their set of feasible actions, players will define a utility function for themselves, which they will try to optimize during the bargaining process.

Third, the disagreement point or the status quo of the game: each bargaining game has a disagreement point that indicates the payoff of each player if the negotiations break down. No player accepts a payoff worse than the one in the disagreement point.

Fourth, the negotiation powers of players: evidently, stronger players want to receive better payoffs in the final solution, and the negotiation powers help differentiate between strong and weak players.

In the disclosure, the bargaining problem is a full-information cooperative game. The 'full-information' setting means that all players know all four pieces of information about all players. The 'cooperative setting' implies that all players are willing to form a grand coalition to obtain higher payoffs compared to the status quo of the game. That being said, in this disclosure, S is the set of all players (which are body organs), X is the set of feasible actions of all players, and $r:=(r_1, \ldots, r_{|S|})$ is the disagreement point where $r_s$ represents the payoff of player $s \in S$ in the disagreement point. Further, $u(d):=(u_1(d), \ldots, u_{|S|})$ can be defined as the vector of non-negative utility functions and $p:=(p_1, \ldots, p_{|S|})$ can be defined as the vector of negotiation powers where $u_s(d)$ and $p_s$ represent the utility function and negotiation power of player $s \in S$, respectively.

3.1 Nash Social Welfare Optimization

In order to find a solution to the bargaining game, a super-criterion can be defined for the problem that can measure the payoff of the grand coalition. To find the optimal grand coalition, the super-criterion can be optimized on the set of all feasible actions. Such super-criteria are often referred to as social welfares in the literature of bargaining problems. In this disclosure, the Nash Social Welfare (NSW) is employed as it can address both efficiency and fairness at the same time when being optimized. Since in the context of the disclosure, each player seeks to minimize its utility function, the Nash solution, denoted by d*, to the bargaining problem can be obtained by solving the following optimization problem, $$d^* \in \operatorname{argmax}\{\Pi_{s \in S}[r_s - u_s(d)]^{p_s} : d \in X, u_s(d) \le r_s \forall s \in S\} \quad \text{Equation 5}$$

In Equation 5, $\Pi_{s \in S}[r_s - u_s(d)]^{p_s}$ is the NSW function, and $[r_s - u_s(d)]$ is the benefit that player $s \in S$ obtains as a result of creating the grand coalition. Note that constraint $u_s(d) \le r_s$ for each $s \in S$ ensures that no player accepts a payoff worse than its guaranteed payoff in the disagreement point. In other words, it guarantees that the benefits have to be non-negative. Also, the benefits are usually from different orders of magnitude, and therefore, comparing different players' benefits can be misleading. As a result, we present the following theorem which says that, by scaling the benefit of any player, an equivalent optimization problem will be created.

Theorem 1. The NSW is scale-free meaning that, by replacing the objective function of Equation 5 by the following function, $$\Pi_{s \in S}[\beta_s r_s - \beta_s u_s(d)]^{p_s},$$

an equivalent problem will be constructed if $\beta_s$ is a positive constant for all $s \in S$.

Following Theorem 1, the benefits of players can be normalized so that they take values between 0 and 1 as follows, $$d^* \in \operatorname{argmax} \left\{ \prod_{s \in S} \left[\frac{r_s - u_s(d)}{r_s - m_s}\right]^{p_s} : d \in X, u_s(d) \le r_s \forall s \in S \right\}. \quad \text{Equation 6}$$

In Equation 6, $$m_s = \min\{u_s(d) : d \in X\}. \quad \text{Equation 7}$$

We refer to $$\left[\frac{r_s - u_s(d)}{r_s - m_s}\right]$$

in Equation 6 as the preference function of player $s \in S$ and assume that $r_s > m_s \ge 0$. Note that if $r_s = m_s$ then player s does not have any flexibility. So, it should be simply removed from the game. The advantage of preference over payoff is that preferences are easily comparable as they are unitless and are from the same order of magnitude. More importantly, unlike payoffs, the preference values are meaningful. Specifically, the value of one for the preference function of player $s \in S$ implies that the obtained solution is 100% similar to the player's ideal outcome that the player is looking for, which is $m_s$. Similarly, the value of zero for the preference function of player $s \in S$ implies that the obtained solution is 100% similar to the player's worse outcome that the player is trying to avoid, which is $r_s$. As an aside, we note that in Equation 6, it is not possible to obtain values worse than $r_s$ for the utility of player $s \in S$ because there is a solid constraint for it. However, there is no constraint to impose that values better/smaller than $m_s$ are not allowed for player $s \in S$. This implies that if, instead of computing $m_s$ exactly, it is simply approximated heuristically, then there will be a chance that the preference functions take values larger than one in theory. In this disclosure, the fluency map optimization problem can be converted to Equation 6 and solve it to find the Nash optimal plan while $m_s$ and $r_s$ are both approximated heuristically for each $s \in S$ based on the outcome of the quadratic fluency map optimization problem. In this disclosure, constraints may not be imposed to bound the utility of player $s \in S$ from below by $m_s$ because by doing so a desirable property of the approach described in Proposition 1 (see Section 5) will no longer hold.

3.2. Approaches

Equation 6 is sometimes referred to as a Maximum Multiplicative Program (MMP). In this disclosure, it is assumed that X is represented by only linear constraints. There are several approaches for solving MMPs, such as using nonlinear solvers or solving the log-transformation form of the problem; however, a more efficient solution approach is to transform the objective function of an MMP into second-order cone constraints. In order to do so, Equation 6 can be reformulated as a geometric-mean optimization as follows, $$\max\left\{\gamma: 0 \leq \gamma \leq \left(\prod_{s \in S}\left[\frac{r_s - u_s(d)}{r_s - m_s}\right]^{p_s}\right)^{\frac{1}{\sum_{s \in S} p_s}}, d \in X, u_s(d) \leq r_s \forall s \in S\right\},$$

where $\gamma$ is a non-negative variable representing the geometric mean of the NSW function. It is evident that optimizing the reformulated problem and having $\gamma'$ as its optimal objective value is the same as optimizing Equation 6 whose optimal objective value will be equal to $\gamma'^{\sum_{s \in S} p_s}$. By letting k be the smallest integer value satisfying $2^k \geq \sum_{s \in S} p_s$ and by introducing a set of non-negative variables and constraints, the geometric mean constraint can be replaced, and the problem can be reformulated as $$\max \gamma$$
$$\text{s.t.: } 0 \leq \gamma \leq \sqrt{\tau_1^{k-1} \tau_2^{k-1}}$$
$$0 \leq \tau_j^l \leq \sqrt{\tau_{2j-1}^{l-1} \tau_{2j}^{l-1}} \text{ for } j = 1, \ldots, 2^{k-l}$$
$$\text{and } l = 1, \ldots, k-1,$$
$$0 \leq \tau_j^0 = \left(\frac{r_s - u_s(d)}{r_s - m_s}\right) \text{ for}$$
$$j = \left(\sum_{l=1}^{s-1} p_l\right) + 1, \ldots, \left(\sum_{l=1}^{s} p_l\right) \text{ and } s = 1, \ldots, |S|,$$
$$0 \leq \tau_j^0 = \gamma \text{ for } j = \left(\sum_{s=1}^{|S|} p_s\right) + 1, \ldots, 2^k,$$
$$d \in X,$$
$$u_s(d) \leq r_s \quad \forall s \in S.$$

Observe that any constraint of the form $\{a, b, c \geq 0: a \leq \sqrt{bc}\}$ is a second-order cone constraint because it is equivalent to $$\left\{a, b, c \geq 0: \sqrt{a^2 + \left(\frac{b-c}{2}\right)^2} \leq \frac{b+c}{2}\right\}.$$

Note that any second-order cone constraint is convex. This combined with the fact that X is assumed to only contain linear constraints suggest that the proposed reformulation can be solved by a convex programming solver as long as u(d) consists of only convex functions. Note that in the reformulation, the only constraint that does not look convex is $$0 \leq \tau_j^0 = \left(\frac{r_s - u_s(d)}{r_s - m_s}\right) \text{ for } j = \left(\sum_{l=1}^{s-1} p_l\right) + 1, \ldots, \left(\sum_{l=1}^{s} p_l\right)$$
$$\text{and } s = 1|S|.$$

However, since the problem is in the form of maximization, the constraint can be written in the form of inequality as follows, $$0 \leq \tau_j^0 \leq \left(\frac{r_s - u_s(d)}{r_s - m_s}\right) \text{ for } j = \left(\sum_{l=1}^{s-1} p_l\right) + 1, \ldots, \left(\sum_{l=1}^{s} p_l\right)$$
$$\text{and } s = 1, \ldots, |S|.$$

This itself is equivalent to
$0 \leq \tau_j^0$ for $j = (\sum_{l=1}^{s-1} p_l) + 1, \ldots, (\sum_{l=1}^{s} p_l)$ and $s = 1, \ldots, |S|$,
$0 \leq r_s - \tau_j^0(r_s - m_s)$ for $j = (\sum_{l=1}^{s-1} p_l) + 1, \ldots, (\sum_{l=1}^{s} p_l)$ and $s = 1, \ldots, |S|$,
$u_s(d) \leq r_s - \tau_j^0(r_s - m_s)$ for $j = (\sum_{l=1}^{s-1} p_l) + 1, \ldots, (\sum_{l=1}^{s} p_l)$ and $s = 1, \ldots, |S|$.

The last constraint is obviously convex if $u_s(d)$ is convex. As an aside, since the linear expression $r_s - \tau_j^0(r_s - m_s)$ is non-negative, it can be replaced by a non-negative (dummy) variable for simplicity (if needed). Also, in the presence of the last constraint (and since by construction $\tau_j^0 \geq 0$, $r_s > m_s \geq 0$, and $r_s - \tau_j^0(r_s - m_s) \geq 0$), the constraint $u_s(d) \leq r_s$ can be removed from the reformulation for each $s \in S$ as they will be redundant. Overall, a nice feature of employing the above-explained transformation is that it can be directly solved by powerful commercial solvers such as CPLEX and Gurobi if u(d) is a vector of linear or convex quadratic functions. That is why this transformation is can be used in this disclosure.

4. EXEMPLARY METHODOLOGY

In this section, an exemplary methodology for transforming a fluency map optimization problem to a bargaining game is provided. As mentioned in Section 2, the transformation in organ level can be performed by considering each organ in patient's body as a player of the bargaining game, which will have |S| players by letting S denote the set of all body organs (under consideration). Body voxels can be categorized into different groups based on the organ that they belong to, and we let $V_s$ represent the set of all voxels in organ $s \in S$, where $V = \cup_{s \in S} V_s$. Moreover, the approach uses a dose prescription and a penalty function for each organ as inputs of the problem. So, $l := (l_1, \ldots, l_{|S|})$ and $u := (u_1, \ldots, u_{|S|})$ can be redefined as the prescription vectors where $l_s$ and $u_s$ show the lower and upper dose level prescribed for organ $s \in S$. As for the penalty function, Section 2 provided that the exemplary methodology is not limited to a specific form of penalty functions. However, the quadratic form of penalty functions is used in this disclosure.

In Problem 3, the general form of the quadratic penalty function is provided for fluency map optimization problems. Note that by dividing voxels into organ categories, Problem 3 can be re-defined, i.e., quadratic fluency map optimization, as $$\min_{d \in \mathcal{D}} \sum_{s \in S} w_s f_s(d) = \sum_{s \in S} w_s (\sum_{v \in V_s} \alpha_v [(d_v - u_s)_+^2 + (l_s - d_v)_+^2]),$$

where $f_s(d)$ is the penalty function of organ $s \in S$. $w := (w_1, \ldots, w_{|S|})$ is also defined as the vector of positive weights where $w_s$ represents the importance of organ $s \in S$. Having the dose prescription and penalty functions provided as inputs, the four pieces of information mentioned are identified in Section 3 to create the bargaining game for the fluency map optimization.

4.1. The Feasible Set of Actions

The feasible set of actions can be defined as $$X := \{d : d \in \mathcal{D}, \hat{l}_s \leq d_v \leq \widehat{u_s} \; \forall v \in V_s \text{ and } \forall s \in S\}. \quad \text{Equation 8}$$

In Equation 8, $\hat{l} := (\hat{l}_1, \ldots, \hat{l}_{|S|})$ and $\hat{u} := (\widehat{u_1}, \cdots, \widehat{u_{|S|}})$ are the vectors of bounds; $\hat{l}_s$ and $\widehat{u_s}$ represent the lower and upper bound for organ $s \in S$, respectively. Observe that the feasible set of actions, X, is precisely the set of all possible fluency maps, i.e., D, with some additional constraints on radiation doses delivered to each voxel within each organ. Note that by replacing $\hat{l}$ and $\hat{u}$ with their prescribed values, i.e., l and u, a feasible set of actions will be exactly the fluency maps that satisfy the prescription. However, as mentioned in Section 2, a common problem with the clinical dose prescriptions is that they are often infeasible, i.e., $X=\emptyset$. This is problematic because, in the bargaining game, each player/organ will start to negotiate from their respective references, and some of the references can be out of reach due to infeasibility. Therefore, to solve this issue, $\hat{l}$ and $\hat{u}$ can be defined such that they are feasible and have the minimal deviation from their initial prescription.

To do so, Equation 9, which is the quadratic fluency map optimization, can be solved to find a feasible solution for the fluency map problem.

$$\tilde{d} \in \operatorname{argmin}_{d \in \mathcal{D}} \{\Sigma_{s \in S} w_s f_s(d)\} \qquad \text{Equation 9}$$

Next, $\hat{l_s}$ and $\hat{u_s}$ can be defined as the minimum and the maximum doses delivered to the voxels of organ $s \in S$ as shown in Equation 10, $$\hat{l_s} = \min_{v \in V_s}\{\tilde{d_v}\}; \; \hat{u_s} = \max_{v \in V_s}\{\tilde{d_v}\}. \qquad \text{Equation 10}$$

Note that, as mentioned earlier, the values defined for $\hat{l}$ and $\hat{u}$ using the exemplary method are feasible and closest to the prescribed values. The vector of weights, i.e., $w := (w_1, \ldots, w_{|S|})$, in Equation 9 can be manipulated to get different $\tilde{d}$ and consequently different $\hat{l}$ and $\hat{u}$. Therefore, if a tighter/looser bound for a specific organ is favorable, one can increase/decrease the organ's weight.

We note that, if the initially prescribed dose levels are certainly feasible, one can use the prescribed dose levels to define the feasible set of actions as shown in $$X := \{d : d \in \mathcal{D}, \, l_s \leq d_v \leq u_s \; \forall v \in V_s \text{ and } \forall s \in S\},$$

Also, one can use the ideal dose levels, i.e., $$l_s = u_s = \begin{cases} 0, & \text{when } s \text{ is } OAR, \\ T_v, & \text{when } s \text{ is } PTV \end{cases}$$

to define the penalty functions. By so doing, the purpose of the bargaining game will be to find a fluency map that is closest to the ideal dose levels but does not violate the prescription.

4.2. Utility Functions

The utility function of organ $s \in S$ is basically its input penalty function, i.e., $f_s(d)$, which is to be minimized. By means of clarity, since quadratic penalty functions are used in this disclosure, the utility function of organ $s \in S$ is $$u_s(d) = f_s(d) = \Sigma_{v \in V_s} \alpha_v[(d_v - u_s)_+^2 + (l_s - d_v)_+^2]. \qquad \text{Equation 11}$$

In Equation 11, $\alpha_v$ is the importance weight of voxel v in organ s, $d_v$ is the total dose delivered to voxel v in organ s, and $l_s$ and $u_s$ are the lower and upper dose levels prescribed for organ s, respectively. The point of considering the penalty functions as our utility functions is that we are designing a bargaining game to find a fluency map that minimizes the deviation from the prescribed dose levels but does not violate the feasible dose levels defined in Section 4.1.

In other words, a fluency map that minimizes the utility/penalty functions of players/organs shown in Equation 11 can be found while satisfying the following constraint, $$\Sigma_{v \in V_s} \alpha_v[(d_v - \widehat{u_s})_+^2 + (\widehat{l_s} - d_v)_+^2] = 0 \; \forall s \in S.$$

4.3. Disagreement Point

This section explains how the payoff of players/organs in the disagreement point can be calculated. The importance of disagreement point is that, in a bargaining game, players/organs will assess their utility/penalty functions with respect to those of other players/organs and will consider a minimum and a maximum expected outcome for themselves. Then, they will not accept any solution resulting in less than their minimum expectation and will try to obtain an outcome as close to their maximum expectation as possible.

Figure 1B:
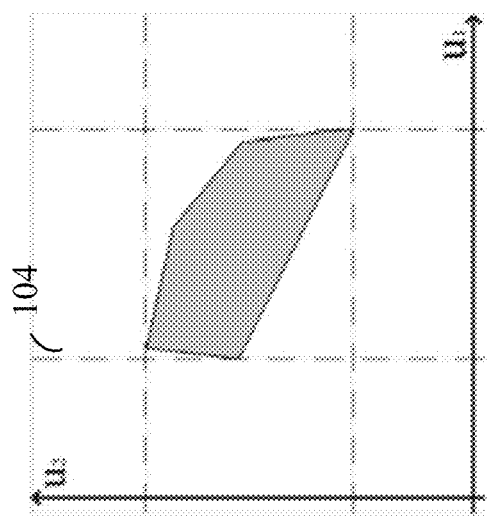
Figure 1A:
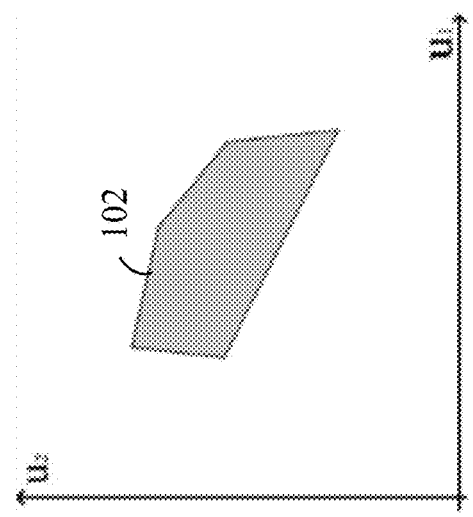

By means of illustration, an example of a bargaining game is provided with two players (|S|=2) trying to minimize their utility functions. FIG. 1a, shows the image of the feasible set of actions 102 in the payoff space, i.e., the feasible values that the utility functions of players can achieve. In FIG. 1b, the dashed lines 104 show the maximum and the minimum values of the utility functions. Since both players try to minimize their respective utility functions, the ideal outcome of the game is when both players achieve their minimum feasible utility, point m 106 in FIG. 1c, and the worst outcome of the game is when both players achieve their maximum feasible utility, point r 108 in FIG. 1c. In other words, point r 108 is the disagreement point of the game, and the players will not accept any solution worse than it. In addition, point m 106 is the ideal point of the game, and the goal of the coalition is to find a final solution that is closest to it.

The process of defining the disagreement point for two-player games (|S|=2) is relatively easy, however as the number of players increases, this process becomes more challenging and computationally expensive. Therefore, we simply propose an approximation technique to compute the disagreement point for fluency map problems.

In the exemplary technique, a pseudo-lexicographic optimization operation can be solved first for each player/organ $s \in S$. Note that a normal lexicographic optimization operation consists of two objective functions: a primary one and a secondary one. The operation seeks to optimize the secondary objective function over all optimal solutions of the primary objective function. The proposed pseudo-lexicographic optimization works similarly but it simply avoids quadratic terms to keep the operation computationally manageable. With this in mind, the operation starts by first solving $$\overline{d^s} \in \operatorname{argmin}_{d \in X}\{u_s(d)\} \qquad \text{Equation 12}$$

and then solving $$\overline{d^s} \in \operatorname{argmin}_{d \in X}\{\Sigma_{s' \in S \setminus \{s\}} u_{s'}(d) : \overline{d_v^s} - \epsilon \leq d_v \leq \overline{d_v^s} + \epsilon \; \forall v \in V_s\}. \qquad \text{Equation 13}$$

Observe that, for each player/organ $s \in S$, two optimization problems can be solved. In the first problem, the player's/organ's utility/penalty function will be minimized on the feasible set of actions defined in Section 4.1. This optimization problem finds the ideal utility/penalty value that the player/organ s can achieve, which is $u_s(\overline{d^s})$. Then, in the second optimization problem, the sum of all other players'/organs' utility/penalty functions will be minimized on the feasible set of actions with some additional constraints. The additional constraints are basically assuring that $u_s(d) = u_s($ $\overline{d^s}$). However, such constraints will add many quadratic terms to the model. So instead, we use the following set of constraints, $$\overline{d_v^s} - \epsilon \leq d_v \leq \overline{d_v^s} + \epsilon \quad \forall v \in V_s,$$

where $\epsilon$ is a sufficiently small positive constant to avoid numerical issues.

By solving the pseudo-lexicographic problem for all players/organs, the ideal expected outcome of each player $s \in S$ is $m_s = u_s(\overline{d^s})$. Therefore, we refer to $\overline{d^s}$ as the ideal fluency map for organ $s$. Note that the ideal fluency map of one organ is not necessarily ideal for other organs since when computing the ideal fluency map for one organ, the other organs are not considered. The worst expected outcome of player $s \in S$ can be estimated by $r_s = u_s(\ddot{d}^s)$, where $$\ddot{d}^s \in \underset{s' \in S}{\operatorname{argmax}} \left\{ u_s(\overline{d})^{s'} \right\}.$$

Therefore, we refer to $\ddot{d}^s$ as the worst fluency map for organ $s$. Note that again the worst fluency map of one organ is not necessarily worst for other organs.

4.4. Negotiation Powers

The vector of negotiation powers, p, provides the practitioners with the ability to further modify the final fluency map by putting more emphasis on an organ by increasing its negotiation power. In other words, having defined the feasible set of actions, utility functions, and the disagreement point, the negotiation powers can help improve the final plan. As mentioned in 2.3, negotiation powers are control levers for the fluency map that, to the best of our knowledge, are introduced in this research for the first time. That said, by developing an update role for negotiation powers, an automated algorithm can be constructed to improve the final plan. The negotiation powers are different from the organs' weights, i.e., w. In particular, the vector w emphasizes the importance of different players/organs in finding the feasible dose levels, where a higher weight results in a tighter dose level. However, the vector p emphasizes the power of player/organ in the bargaining process, where a higher power results in a final solution more preferable for the player/organ.

4.5. Fluency Map Bargaining Game

Sections 4.1-4.4 explain the exemplary methodology to define the necessary pieces of information to create a bargaining game. Now, we formally define the fluency map bargaining game based on Equation 6 as the following optimization problem $$\max \prod_{s \in S} \left[ \frac{r_s - u_s(d)}{r_s - m_s} \right]^{p_s} \quad \text{Equation 14}$$

s.t. $u_s(d) \leq r_s \quad \forall s \in S,$ $d_v = \sum_{n \in N} D_{vn} x_n \quad \forall v \in V,$ $\hat{l}_v \leq d_v \leq \hat{u}_v \quad \forall v \in V,$ $x_n \geq 0 \quad \forall n \in N.$ To find the Nash optimal solution of the fluency map bargaining game, practitioners can use the approach explained in Section 3.2 to convert the objective function of Equation 14 into second-order cone constraints and then solving the reformulation using commercial solvers such as CPLEX and Gurobi. In terms of implementation, as mentioned in Section 3.2, for each $s \in S$, when applying the transformation the constraint $u_s(d) \leq r_s$ will become redundant and can be removed. Additionally, we know that by construction, when computing $m_s$ and $r_s$, where $s \in S$, the constraint $\widehat{l_v} \leq d_v \leq \widehat{u_v}$ is considered for each $v \in V$. This combined with the fact that $u_s(d) \leq r_s$ for each $s \in S$ suggest that when solving the optimization problem, most likely the constraint $\widehat{l_v} \leq d_v \leq \widehat{u_v}$ will be naturally satisfied for each $v \in V$. This is because the optimization problem attempts to make $u_s(d)$ closer to $m_s$ for each $s \in S$. Therefore, during the course of this research, we found out that it is computationally significantly better to remove the constraint $\widehat{l_v} \leq d_v \leq \widehat{u_v}$ for each $v \in V$ when solving the fluency map bargaining game. Note that by removing these constraints, $m_s$ is no longer a true lower bound for the utility of organ $s \in S$, i.e., it will become an approximate bound. So, in that case, based on the discussions in Section 3, it is possible that preference functions take values larger than one in theory, however that would be unlikely in practice. Removing these constraints also has an important theoretical advantage that will be discussed in the next section, see Proposition 1.

5. THEORETICAL DISCUSSION

This section explores an exemplary fluency map bargaining game (in Section 4.5) from the theoretical perspective. To do so, some concepts can be first introduced from the field of multi-criteria optimization as it is known that radiotherapy treatment planning has a strong connection with this field. Specifically, it is known that most existing methods for the fluency map optimization problem can be viewed as different approaches for solving the following multi-criteria optimization problem, $$\min_{d \in \mathcal{D}} \{f_1(d), \ldots, f_{|S|}(d)\}.$$

Recall that $f_s(d)$ is the penalty/objective function defined for organ $s \in S$. Unfortunately, due to the conflicting nature of the objective functions, it is often impossible to find a feasible solution, i.e., fluency map, that can minimize all penalty functions simultaneously. Hence, the goal of many existing state-of-the-art techniques, when solving the fluency map optimization problem, is to find a Pareto-optimal solution (see Definition 1) that can desirably balance the conflicts between the objectives.

A feasible fluency map, $\hat{d} \in \mathcal{D}$, is Pareto-optimal if there exists no other feasible fluency map, $d' \in \mathcal{D}$, such that $f_s(d') \leq f_s(\hat{d}), \forall s \in S,$ $f_s(d') < f_s(\hat{d}), \exists s \in S.$ In the radiotherapy field, there are two main categories of solution methods for computing a desirable Pareto-optimal solution for the fluency map problem. These two categorizes are referred to as non-automated and automated in this paper, and the main difference between them is that the level of interactions with decision maker(s) is more significant in the non-automated approaches. Specifically, in the non-automated approaches, the focus is on generating the entire set or a large subset of Pareto-optimal solutions in order to enable decision makers to navigate through them and identify a desirable solution. As an aside, some existing commercial treatment planning software, e.g., RayStation, are developed based on the non-automated approaches. Although the non-automated approaches are a valuable source for understanding the trade-offs between the conflicting objectives, they have two main disadvantages. First, computing the entire set (or a large subset) of Pareto-optimal solutions can be computationally expensive, i.e., time consuming. The second disadvantage is that it is long argued in the field of multi-criteria optimization that presenting too many Pareto-optimal solutions to decision makers can sometimes confuse the decision makers and make selecting a preferred solution difficult. So, the process of selecting a desirable Pareto-optimal solution itself can be burdensome as well.

To overcome the above-mentioned challenges, the automated solution approaches seek to directly return a desirable Pareto-optimal solution based on the decision maker's wish-list, which is a solution-approach and decision-maker dependent list including information such as the priority of each objective, their corresponding acceptable values, etc. In other words, in the context of the automated solution approaches, a desirable Pareto-optimal solution can be viewed as the closest solution to the wish-list of decision makers (rather than a solution that decision makers select by inspection). Since there is no unique and trivial way to measure the closeness, identifying the closest solution is not a trivial task too. Consequently, not surprisingly, several automated solution approaches exist in the literature. In fact all the solution approaches that we discussed through this paper, e.g., the quadratic fluency map optimization or our proposed fluency map bargaining game, belong to the category of automated solution approaches. Two other approaches in the same category are the so-called lexicographic optimization method and the 2-phase e-constraint method; these two methods can be used in a computational study.

All automated solution approaches seek to minimize the level of interactions with decision makers in order to speed up the entire planning process. However, if decision makers are not happy with the plan generated by an automated solution approach, they still have the option to make changes to their wish-lists in order to force the approach to return a possibly different solution. Of course, the hope of all automated solution approaches is to avoid such an interactive process (or minimize the number of iterations). In the context of our approach, the wish-list can be viewed as the negotiation powers, weights, etc. With this in mind, it can be proven that the approach in the disclosure is indeed an automated solution approach. In order to do so, it suffices to prove that the proposed approach always returns a Pareto-optimal solution. The approach comes with an additional natural advantage which makes its outcome likely to be acceptable for decision makers.

Proposition 1. The Proposed Fluency Map Bargaining Game, i.e., Equation 14, Always Returns a Pareto-Optimal Solution.

Proof Recall that in the context of this disclosure, $u_s(d) = f_s(d)$ for each $s \in S$, see Section 4.2. Moreover, based on the discussions in Section 4.5, the constraint $l'_v \le d_v \le u'_v$, should be removed from Equation 14 for each $v \in V$. So, the proposed fluency map bargaining game can be stated as $$\max \prod_{s \in S} \left[ \frac{r_s - f_s(d)}{r_s - m_s} \right]^{p_s}$$

-continued $$\text{s.t.} \quad f_s(d) \le r_s \quad \forall s \in S,$$

$$d \in \mathcal{D}.$$

The assertion by contradiction can be proven. Let d* be an optimal solution of the above-mentioned problem and suppose that it is not Pareto-optimal. In that case, following Definition 1, there may exist a solution, d'∈D, that dominates d*, i.e., $$f_s(d') \le f_s(d^*) \quad \forall s \in S,$$

$$f_s(d') < f_s(d^*) \quad \exists s \in S.$$

First note that since $f_s(d^*) \le r_s$ for all $s \in S$, $f_s(d') \le r_s$ may be given for all $s \in S$. This is because otherwise (by definition) there must exist $s \in S$ such that $f_s(d^*) \le r_s \le f_s(d')$ which clearly violates the assumption that d' dominates d*. This combined with the fact that d'∈D imply that d' is a feasible solution for the proposed fluency map bargaining game. Now, since by assumptions $r_s > m_s \ge 0$ for all $s \in S$, the equation below is given.

$$\prod_{s \in S} \left[ \frac{r_s - f_s(d^*)}{r_s - m_s} \right]^{p_s} < \prod_{s \in S} \left[ \frac{r_s - f_s(d')}{r_s - m_s} \right]^{p_s}.$$

Consequently, d* cannot be an optimal solution as d' has a better objective value for the fluency map bargaining game (a contradiction).

Following Proposition 1, as long as the assumption $r_s > m_s \ge 0$ and $p_s > 0$ for all $s \in S$ hold, the returned solution by solving the proposed fluency map bargaining game is definitely Pareto-optimal. So, in essence, users have the full flexibility to choose any arbitrary values for those parameters in a clinical setting. The only consideration is that due to the existence of the constraint $f_s(d) \le r_s$ for all $s \in S$ in the fluency map bargaining game, there is a possibility that the fluency map bargaining game becomes infeasible for some arbitrary choices of the disagreement point. That is the main reason that in the exemplary proposed approach, 2|S|+1 optimization problems can be solved to compute the disagreement points such that the fluency map bargaining game remains feasible.

In addition to the Pareto-optimality, the exemplary approach comes with a unique desirable property which is balancing efficiency and fairness. Intuitively, efficiency means maximizing the total size of the cake while fairness means dividing/sharing the cake as equitable as possible among players with respect to their negotiation powers, i.e, those with higher negotiation powers are likely to get a larger proportion of the cake. In the context of our research, the 'cake' refers to any feasible treatment plan; the share of a player/organ from the cake refers to the similarity ratio of the treatment plan to its ideal plan; and finally, the size of the cake is the sum of all similarity ratios.

In a perfect world, each organ will receive a radiation plan which is 100% similar to its true ideal plan. However, that may not be achievable in practice, and therefore, there can be trade-offs between fairness and efficiency. Given the disagreement point and negotiation powers of players, in the field of game theory, a natural way of balancing efficiency and fairness is to maximize the NSW function over the feasible set of actions. In other words, by maximizing the NSW function, we are implicitly trying to find a solution/plan that maximizes the size of the cake. If by so doing, it turns out that the cake is divided completely fairly then that solution has to be optimal. Otherwise, the approach implicitly attempts to give up on the size of the cake in order to improve fairness. Overall, balancing efficiency and fairness is an important property of our approach as it suggests that our proposed approach naturally attempts to avoid generating extreme Pareto-optimal solutions/plans which are significantly biased towards some players (unless their negotiation powers are considerably higher). This is desirable as such extreme plans are typically unacceptable for decisions makers.

6. NUMERICAL RESULTS

In this section, a numerical study is conducted by implementing the proposed bargaining game on the TG-119 and the liver case provided in a dataset. For each case study, the results are compared with a state-of-the-art solution approach, i.e., quadratic fluency map optimization, in this section. Note that the quadratic fluency map optimization is precisely Equation 9. In the numerical study, the weights are considered in organ level, i.e., w, and negotiation powers, i.e., p. Therefore, the voxel-level importance weights are not considered, i.e., $\alpha_v=1$ for each $v \in V$. For both case studies, the ideal dose prescription of the form was followed $$l_s = u_s = \begin{cases} 0, & \text{when } s \text{ is OAR,} \\ T_v, & \text{when } s \text{ is PTV} \end{cases}$$

where OAR includes all healthy organs of the body and PTV are the cancerous organs to be eliminated. Note that the organ weights, w, play an important role in defining the feasible set of actions of the bargaining game. Therefore to conduct a more comprehensive numerical study, two different cases are considered for them. Specifically, for the TG-119 case, organ weights are selected such that they prioritize OAR sparing over PTV coverage. However, for the liver case, the organ weights are selected to prioritize PTV coverage over OAR sparing. The exemplary methodology was implemented in C++ and used CPLEX 12.9 as the solver. The computational experiments are conducted on a Dell PowerEdge R360 with two Intel Xeon E5-2650 2.2 GHz 12-Core Processors (30 MB), 128 GB RAM, the RedHat Enterprise Linux 6.8 operating system, and using the default settings of CPLEX.

6.1. TG-119 Case

For TG-119 case, we used all the five beam angles provided in a dataset. The case includes a total of 418 beamlets, a total of 599,440 body voxels, and three body organs. The organs are Target with 7,429 voxels, Core with 1,280 voxels, and Normal tissues with 302,953 voxels. Note that the remainder of 287,778 body voxels receive a maximum of zero radiation, and therefore, we did not include them in the model and in the DVH. We assumed a prescription dose of 55 Gray (Gy) for the Target. To prioritize Core sparing over PTV coverage, and PTV coverage over body sparing, we simply considered organ weights relative to the organs' sizes as follows, $$w_C = \frac{1}{1,280}, w_T = \frac{1}{7,429}, w_N = \frac{1}{287,778},$$

where $w_C$, $w_T$, and $w_N$ are the importance weights of Core, Target, and Normal tissues, respectively.

Following Remark 1, these bounds result in the tightest dose levels for Core and the loosest dose levels for Normal tissues. The steps in Section 4.1 were followed to define the feasible set of actions and to calculate the feasible dose levels for each player/organ, which are provided in Table 1.

TABLE 1

TG119 case: Feasible dose levels

| | l' | u' |
|---|---|---|
| Core | 0.56 | 15.09 |
| Target | 31.25 | 64.46 |
| Normal | 0.0 | 55.90 |

Figure 2:
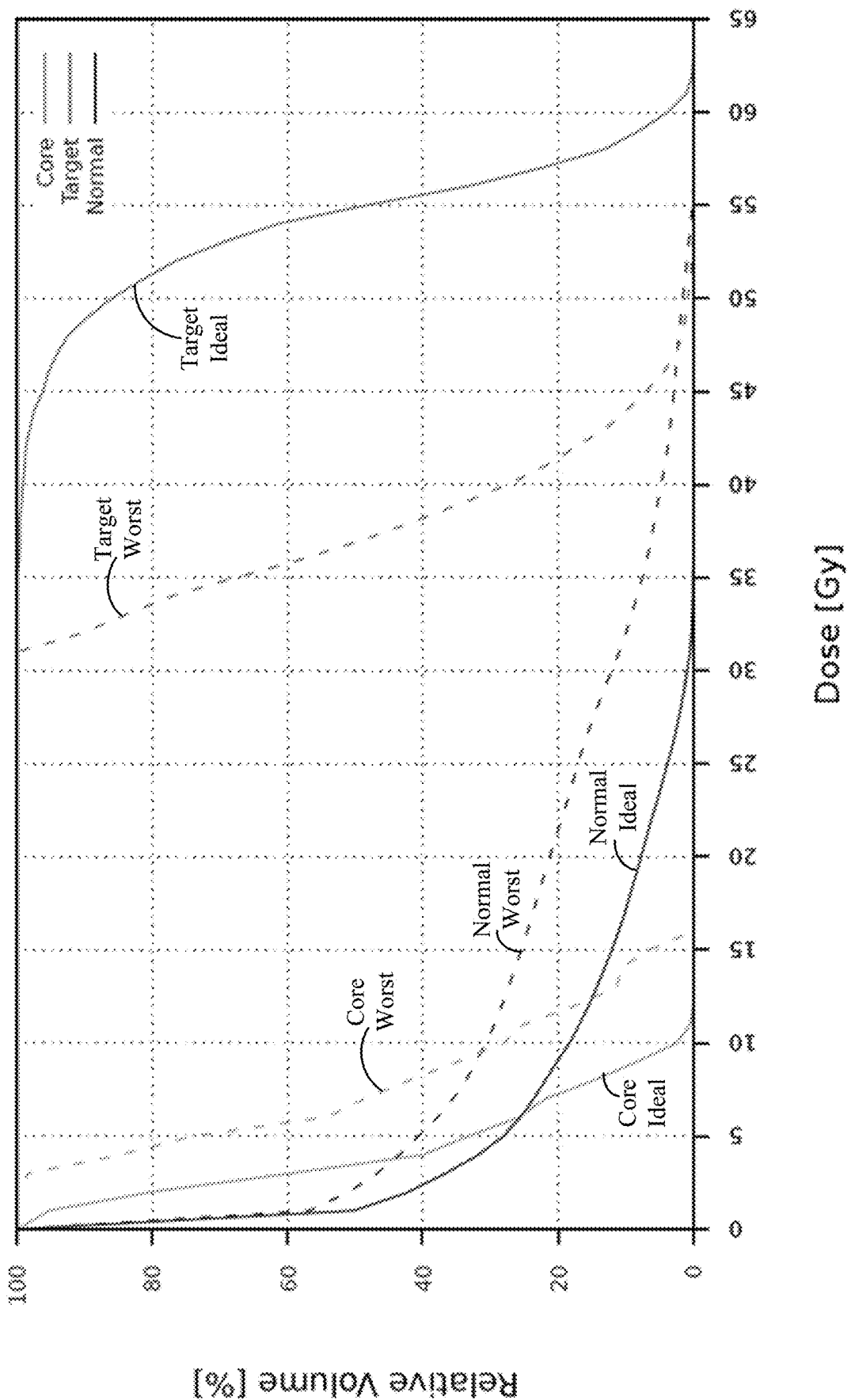
FIG. 2 is an illustration of an example of TG-119 case: Dose Volume Histogram (DVH) of the ideal and worst utility/penalty values according to some embodiments.

Following Section 4.3 to define the disagreement point, we calculated the ideal and worst expected utility/penalty values for each player/organ. FIG. 2 depicts the DVH of the ideal (solid line) and the worst (dashed line) fluency maps of each player/organ. Note that for each organ $s \in S$, its ideal DVH can be generated based on $\overline{d}^s$ as it corresponds to $m_s$ (which is its expected ideal outcome) and also its worst DVH can be generated based on $\ddot{d}^s$ as it corresponds to $r_s$ (which is its expected worst outcome). Note that in FIG. 2, the area between the ideal and the worst DVH of each player/organ provides the range where the solution of our Nash Social Welfare optimization is expected to lie in.

FIG. 2 helps to have an overview of the outcome of the bargaining game. As mentioned in Remark 2, the negotiation powers of players/organs determine their similarity to their ideal expected outcome. Therefore, for example, by using a sufficiently large negotiation power for Target compared to the powers of Core and Normal tissues, one can obtain a Target DVH identical to its solid line in FIG. 2. However, in such a case, a DVH similar to the dashed lines should be expected for Core and Normal tissues. By means of clarification, we modeled the bargaining game testing different negotiation powers. The powers we tested are $(p_T, p_C, p_N) \in \{(1, 1, 1), (21, 1, 1), (42, 1, 1), (42, 10, 1)\}$, where the highest power is related to Target and is approximately equal to the ratio of the total number of body voxels divided by number of Target voxels. Specifically, these powers were chosen to show the changes in the outcome of the game as the negotiation power of Target gradually increases. To compare the result of the approach with the quadratic fluency map optimization, in FIG. 3, the DVH generated by employing the tested negotiation powers in bargaining game was provided as solid lines and the DVH of the quadratic fluency map optimization, i.e., Equation 9, as dashed lines.

Figure 3A:
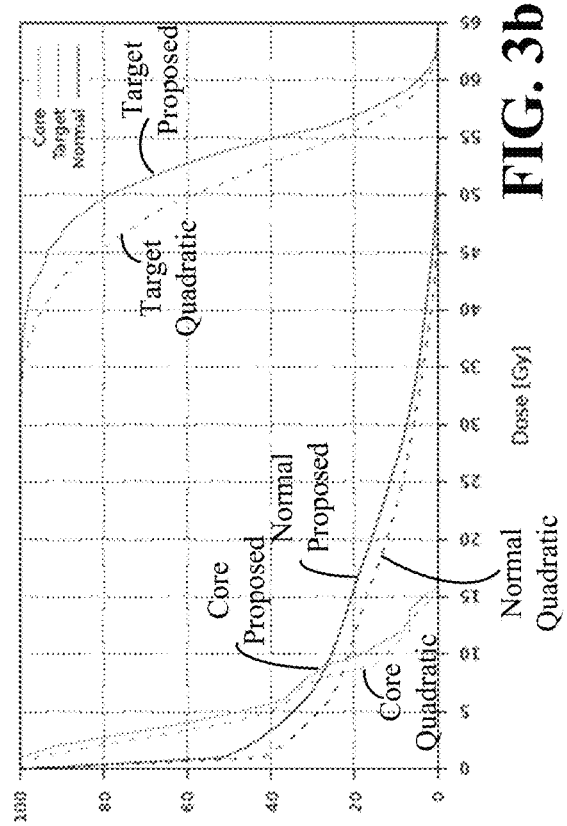
FIGS. 3a-3d are an illustration of an example of TG-119 case: DVH comparison between the Nash optimal solution and the quadratic optimal solution according to some embodiments.

FIG. 3a with powers $(p_T, p_C, p_N)=(1, 1, 1)$ shows the DVH of the game where all players/organs have unit powers. The outcome of the bargaining problem (solid lines) shows 75\%, 90.11\%, and 74.9\% similarity of Target, Core, and Normal to their ideal expected utility/penalty values, respectively. Note that these are the values of preference functions explained in Section 3.1 (that are multiplied by 100) after solving the bargaining problem. The similarity percentages of the outcome of the fluency map optimization problem (dashed lines) can be also obtained by plugging its solution into the preference functions explained in Section 3.1. By doing so, the percentages will be 88.7\%, 70.4\%, and 66.5\% for Target, Core, and Normal respectively. This indicates that in the bargaining process, the preference of Target is sacrificed to obtain the maximum NSW.

Figure 3B:
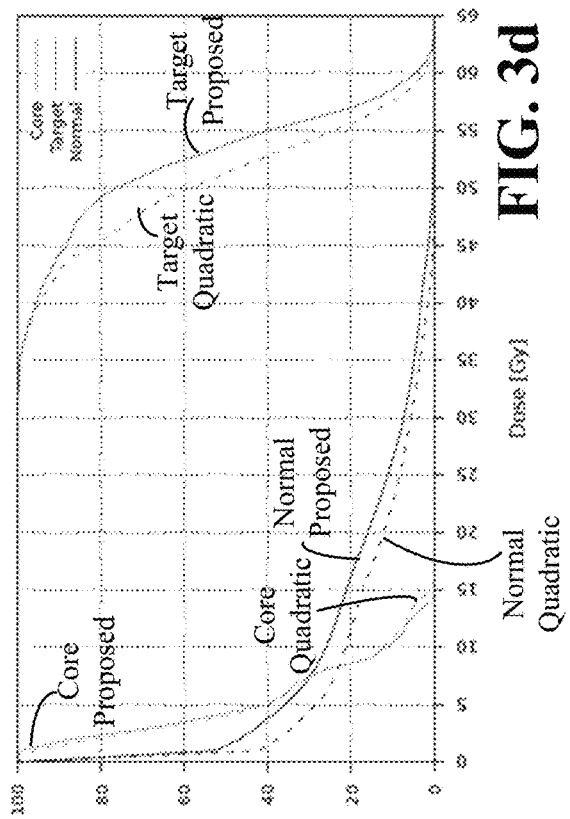
Figure 3C:
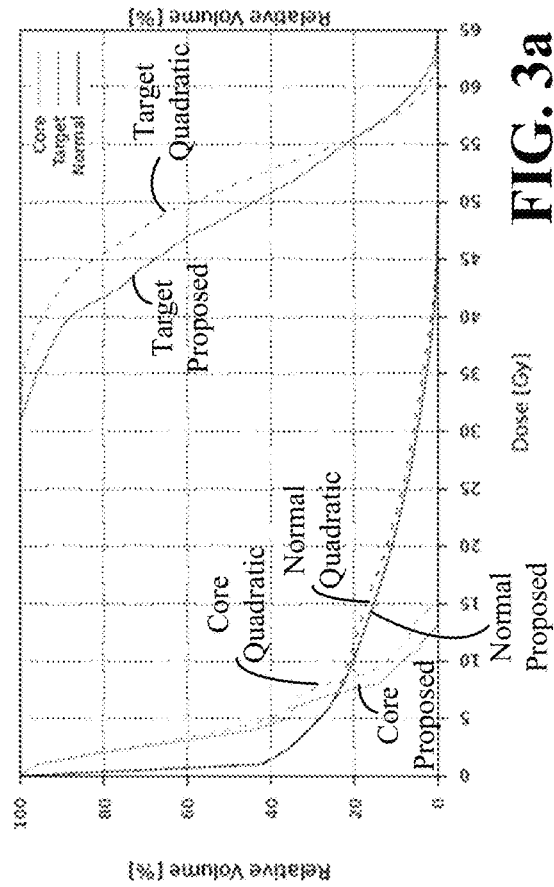

FIG. 3b with powers $(p_T, p_C, p_N)=(21, 1, 1)$ and FIG. 3c with powers $(p_T, p_C, p_N)=(42, 1, 1)$ show the DVH of the game where the negotiation power of Target is increased to 21 and 42, and Core and Normal have unit powers. These games resulted in 97.01\% and 97.93\% similarity of Target to its ideal case. The similarity percentages of Core are 55.8\% and 48.92\%, and of Normal are 41.7\% and 34.32\%. Observe that, as the negotiation power of Target is increased in comparison to the power of other players/organs, the preference value of Target increases, and it tends to obtain a DVH closer to its ideal DVH. However, the preference of other players/organs decreases, and their DVH moves closer to their worst case.

Figure 3D:
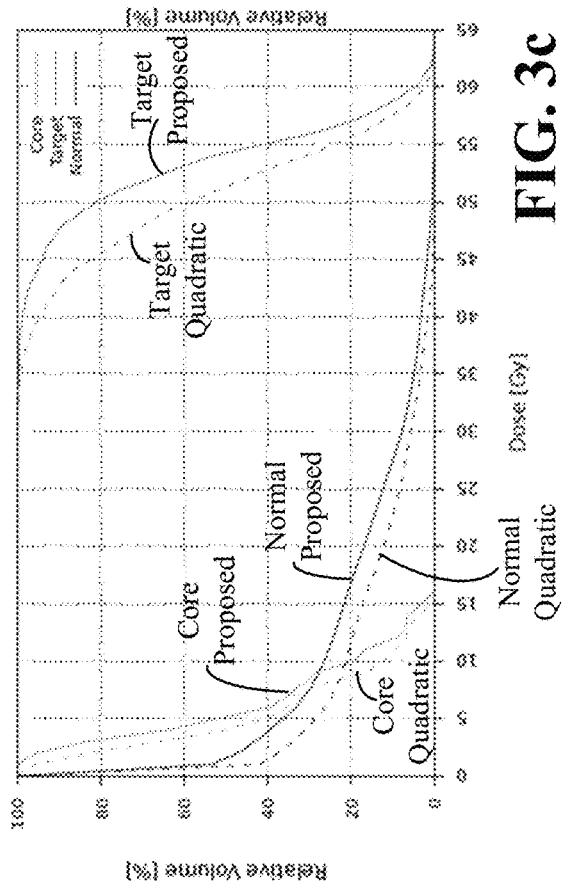

FIG. 3d shows the case where Target has a power of 42, Core has a power of 10, and Normal has unit power. In this case, the similarity of Target, Core, and Normal to their ideal case are 93.6\%, 73.3\%, and 39.2\%, respectively. It is clear that, due to the negotiation powers, the preference of Normal is sacrificed to ensure a higher preference for Target and then Core. Similarly, we observe from FIG. 3d that the DVH of Core and Target has changed for the better by sacrificing the DVH of Normal compared to their DVH's generated by the quadratic fluency map optimization.

6.2. Liver Case

This section implements the exemplary methodology on the liver case provided in the dataset. In this dataset, a total of 56 beam angles are provided, of which we only use 8 that are reported as the result of the beam angle optimization algorithm. These 8 beam angles include a total of 519 beamlets. The body organs that we include in our model are PTV with 6,954 voxels, Skin with 465,093 voxels, Heart with 28,867 voxels, Left Kidney (KidneyL) with 1,295 voxels, Right Kidney (KidneyR) with 692 voxels, Large Bowel with 133 voxels, Liver with 52,999 voxels, Spinal Cord with 685 voxels, and Stomach with 7,789 voxels. Therefore, the total number of body voxels are equal to 564,507, all of which can receive a maximum dose of greater than zero by the included beam angles.

Since the liver case is more realistic compared to TG-119, we divide our numerical analysis in this section into two parts. In the first part, we provide an overview of the performance of the proposed algorithm compared to the quadratic optimization similar to what we did for the TG-119 case. In the second part, a performance comparison is provided between our proposed algorithm and two existing automated (multi-criteria) solution approaches including lexicographic optimization method (Lexico) and the 2-phase ε-constraint method (2pεc). The specific implementation of Lexico and 2pεc on the liver case is provided at Section 8.

6.2.1. Overall Performance

Figure 4:
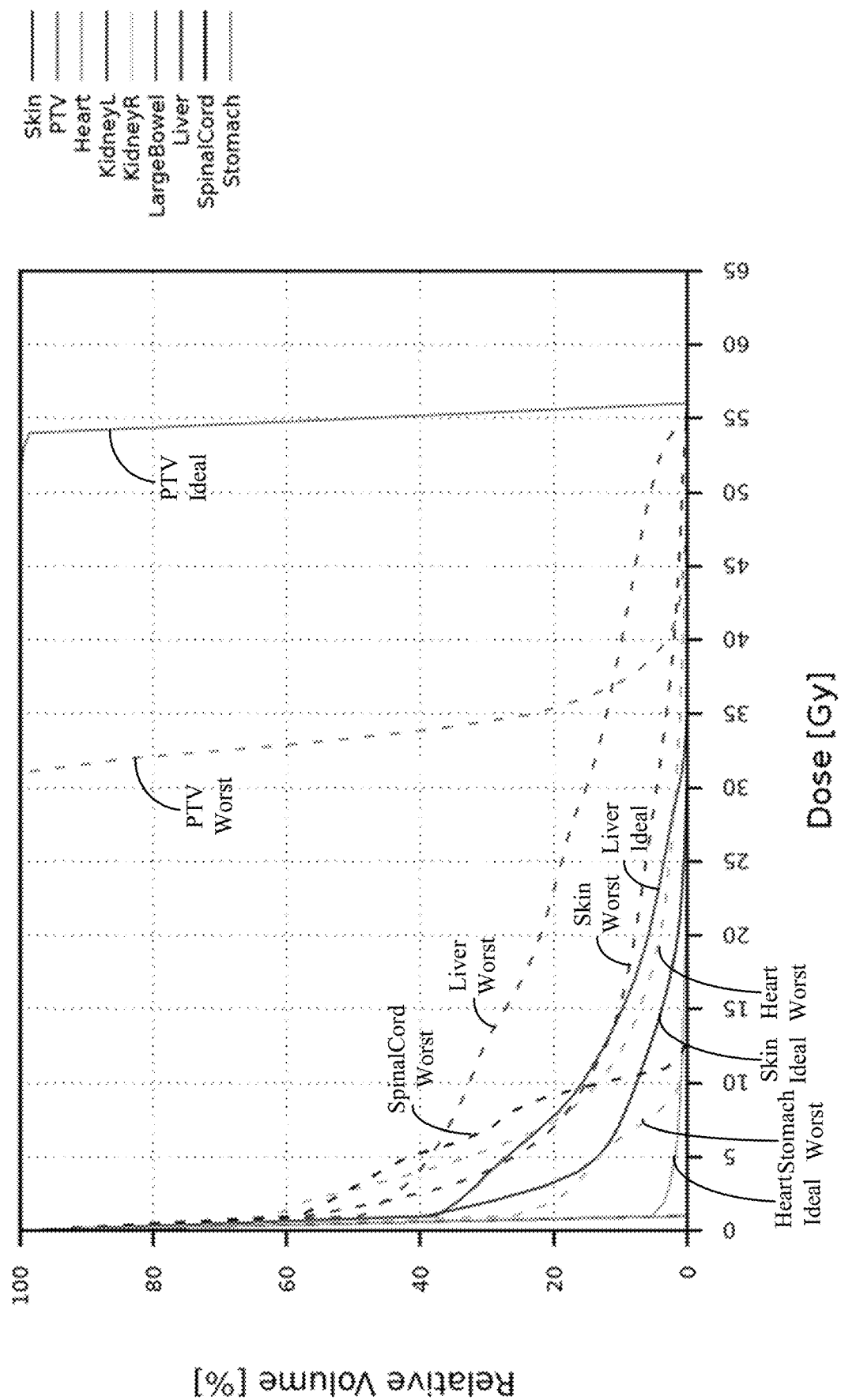
FIG. 4 is an illustration of an example of liver case: DVH of ideal and worst utility/penalty values according to some embodiments.

Similar to the TG-119 case, we assume a prescription dose of 55 Gy for the PTV and zero Gy for other organs, and unlike to the TG-119 case, the feasible bounds that prioritize PTV coverage over OAR sparing were found. To do so, the following importance weights were employed, $$w_s = \begin{cases} \frac{6,954}{564,507} & s = PTV \\ \frac{1}{564,507} & \text{otherwise} \end{cases}$$

where $w_{PTV}$ is the ratio of the PTV size to the total number of voxels, and other weights are the ratio of one over the total number of voxels. Then, the feasible dose levels of each player/organ following Section 4.1 were defined, which are provided in Table 2. Further, in the process of defining the disagreement point, the DVH of the ideal and worst expected utility/penalty values were extracted for each player/organ, which are provided in FIG. 4.

TABLE 2

| Liver case: Feasible dose levels | | |
|---|---|---|
| | l' | u' |
| PTV | 31.31 | 59.73 |
| Skin | 0.0 | 58.24 |
| Heart | 0.0 | 50.47 |
| KidneyL | 0.0 | 0.03 |
| KidneyR | 0.0 | 0.06 |
| Large Bowl | 0.0 | 0.02 |
| Liver | 0.0 | 55.14 |
| Spinal Cord | 0.0 | 12.14 |
| Stomach | 0.0 | 15.15 |

Similar to the previous section, we modeled the bargaining game using different negotiation powers, where the highest power is related to PTV which is approximately equal to the ratio of the total number of body voxels to the number of PTV voxels. FIG. 5 compares the DVH of the Nash optimal solutions with the tested negotiation powers (solid lines) with the DVH of the quadratic fluency map optimization (dashed lines). FIG. 5a shows the DVH of the game where all players/organs have the same unit powers. From this figure, we observe that, similar to the TG-119 case, the preference of PTV is sacrificed to obtain the maximum NSW. Moreover, the DVH of Skin has changed a little compared to the quadratic optimal solution, but the DVH of all the other players/organs have improved.

Figure 6A:
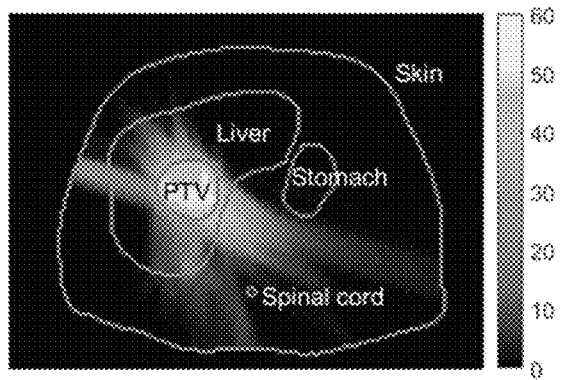
FIGS. 6a-6d are an illustration of an example of liver case: dose distribution map of the Nash optimal solution according to some embodiments.
Figure 6B:
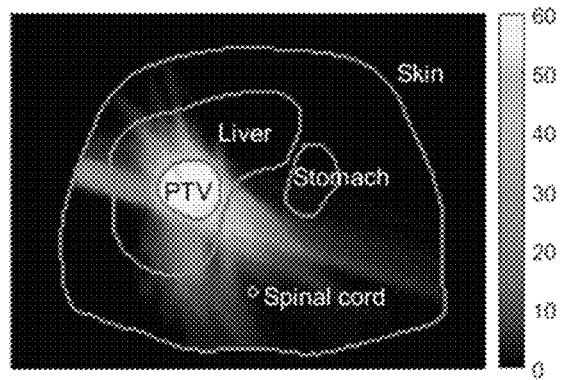
Figure 6C:
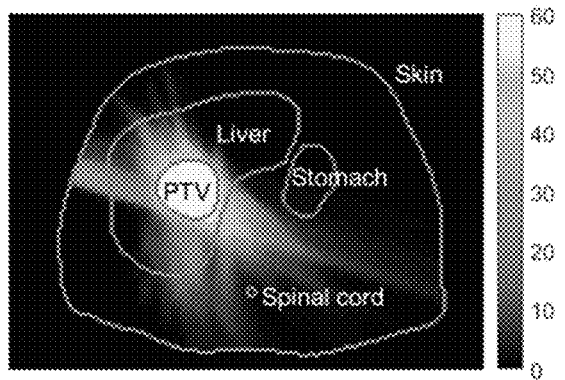
Figure 6D:
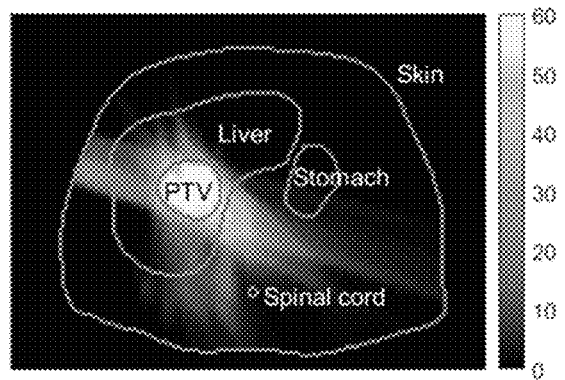

FIGS. 5b and 5c show the DVH of the Nash optimal solution where PTV has a negotiation power equal to 40 and 81, and the other players/organs have powers equal to one. Observe that, as the negotiation power of PTV increases, its DVH tends to move closer to its ideal case. During this change, although the quadratic fluency map optimization resulted in a better DVH for Skin and Liver, the Nash optimal solution resulted in highly improved DVH's for all other organs. FIG. 5d shows the DVH of the Nash optimal solution where PTV has a negotiation power equal to 81, Liver has a power equal to 10, and the rest of the players/organs have unit powers. Observe from FIG. 5d that the bargaining game has improved the DVH of all players/organs compared to the quadratic optimal solution with the cost of slightly sacrificing the DVH of Skin. Finally, since the liver case is more realistic (compared to TG-119), for interested readers, we report a 2D dose distribution map of its Nash optimal solution in FIG. 6 for all four scenarios of negotiation powers. Here, FIG. 6a includes $p_s=1$ for all organs, FIG. 6b includes $p_{PTV}=40$ and $p_s=1$ for others, FIG. 6c includes $p_{PTV}=81$ and $p_s=1$ for others, and FIG. 6d includes $p_{PTV}=81$, $p_{Liver}=10$, and $p_s=1$ for others.

6.2.2. Performance Comparison

We now compare the performance of our approach with the Lexico and 2pεc. The wish-list that we use for the Lexico and 2pεc is summarized in Table 3. The wish-list is designed based on the outcome of the proposed approach in FIG. 5d. In other words, the wish-list is defined in such a way that the performance of the approach shown in FIG. 5d is compared with the Lexico and 2pεc. Since in FIG. 5d, the PTV has the highest negotiation power, we give the first priority to the PTV in the Lexico and 2pεc. Moreover, since the liver has the second highest negotiation power in FIG. 5d, the second highest priority is given to the liver. Finally, since all other organs have the same negotiation powers in FIG. 5d, the third priority is given to all other organs together. In FIG. 5d, the (quadratic) penalty value for the PTV is 68,386.38, so we set 68,386.38 as the goal for the PTV. Similarly, the (quadratic) penalty value for the liver is 8,750,124.63 in FIG. 5d, so 8,750,124.63 was set as the goal for the liver. Finally, the sum of all (quadratic) penalty values for other organs is 42,012,837.22 in FIG. 5d, so 42,012,837.22 was set as the goal for the all other organs together.

TABLE 3

Liver case: the wish-list used for Lexico and 2pεc

| Priority | Volume | Goal |
| --- | --- | --- |
| 1 | PTV | 68,386.38 |
| 2 | Liver | 8,750,124.63 |
| 3 | Other organs | 42,012,837.22 |

As an aside, in order to employ Lexico and 2pεc, Gurobi 9.1 was used. FIG. 7 compares the DVH of the outcomes of the Lexico and 2pεc (dashed lines) with the outcome of the proposed bargaining game (solid lines). From FIG. 7a, the Lexico has resulted in an extreme solution that is mostly preferable to the PTV. Observe that the DVH of PTV in this figure is almost the same as its expected ideal DVH in FIG. 4 while other organs are receiving doses close to their worst expected DVH. In fact, some organs (e.g., the spinal cord) are receiving DVH which is worse than our worst expected DVH. Note that this is possible because our worst expected DVH is defined based on our proposed Nash bargaining approach, i.e., the disagreement point. Therefore, since the concept of disagreement point does not exist in the other approaches, there is no guarantee that they do not violate it.

Figure 8A:
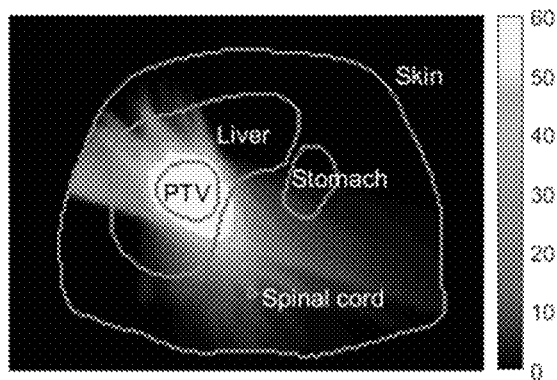
FIGS. 8a-8b are an illustration of an example of liver case: dose distribution map of the treatment plans generated by Lexicographic optimization or 2pεc approach according to some embodiments.
Figure 8B:
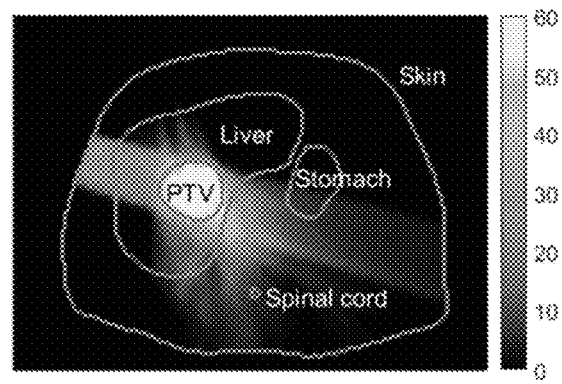

By comparing FIGS. 7a and 7b, we observe that the plan generated by 2pεc is significantly less extreme than the one generated by Lexico. While the plan generated by 2pεc is favorable towards skin, we observe that its negative impacts on some organs (e.g., heart, spinal cord, and stomach) are more significant than the plan generated by the Nash bargaining solution. In other words, although the wish-list is designed to guide the Lexico and 2pεc to create plans similar to the one generated by our proposed bargaining game, they ended up creating more extreme solutions compared to the proposed approach. This is mainly because as mentioned in Section 5, the proposed fluency map bargaining game naturally seeks to generate a Pareto-optimal plan that can balance the efficiency and fairness based on the parameters that users provide. However, such a process does not naturally exist in other solution approaches. So, users need to manually achieve that by exploring different parameters settings (e.g., different wish-lists). Finally, similar to the previous subsection, for interested readers, we report a 2D dose distribution map of the Nash optimal solution for both the Lexico and 2pεc in FIG. 8. Similar conclusions to the above-mentioned ones can be made by comparing FIGS. 6d, 8a, and 8b.

7. CONCLUSION

In this disclosure, a methodology that, for the first time, models a fluency map problem as a game is discussed. Specifically, a bargaining game is discussed where players/organs start bargaining from their worst expected DVH and try to get a final solution closer to their ideal plan. During this process, the fluency map optimization is redefined such that, instead of the typical penalty functions, new objective functions referred to as preference functions are suggested. The advent of preference functions has several advantages. First, the preference values of all organs are unitless and are expected to be in the range of zero to one, which makes the objective values comparable to each other. Second, the values of the new functions are meaningful as they represent the similarity percentage of each player's/organ's plan to its ideal plan.

Further, to assure the efficiency and mathematically provable fairness of the final solution of our proposed game, the concept of Nash Social Welfare is used in the exemplary methodology. The use of Nash Social Welfare enabled a new control lever for the fluency map optimization, the so-called negotiation powers. These powers control the similarity rate of each player/organ to their ideal plan in the final solution and provide the flexibility of putting more emphasis on an organ by increasing its negotiation power.

8. APPENDIX

This section provides the details of how to specifically implement Lexico and 2pεc on the liver case, i.e., Section 6.2. Before doing so, we provide some notations to facilitate the presentation. First note that based on the wish-list given in Table 3, three penalty objectives should be created. The first one belongs to the PTV (which has the highest priority), the second one belongs to the liver (which has the second highest priority), and the last one belongs to all other organs together (which means that none of the other organs has priority over each other). With this in mind, we denote the objective with priority $i \in \{1,2,3\}$ by $\bar{f}_i(d)$ and define them as follows, $$\bar{f}_1(d) := \Sigma_{v \in V_{PTV}}(d_v - 55)^2,$$

$$\bar{f}_2(d) := \Sigma_{v \in V_{Liver}}(d_v - 0)^2,$$

$$\bar{f}_3(d) := \Sigma_{s \in S/PTV,Liver} \Sigma_{v \in V_s}(d_v - 0)^2.$$

The goal values given in Table 3 by g, for each $i \in \{1,2,3\}$. Specifically, we have that, $g_1 = 68,386.38$, $g_2 = 8,750,124.63$, $g_3 = 42,012,837.22$.

Finally, we define δ as a constant slightly greater than one to avoid numerical issues in Lexico and 2pεc. In the implementation, $\delta = 1.03$ is set.

Appendix A.1. Lexico

The Lexico contains three main steps and in each step, one optimization problem needs to be solved. The first step optimizes the penalty function with the highest priority over all feasible solutions, i.e., $\bar{f}_1^* := \min\{f_1(d): d \in \mathcal{D}\}$.

In the second step, the second penalty function is optimized over all feasible solutions that are optimal for the first objective, $\bar{f}_2^* := \min\{f_2(d): f_1(d) \leq \bar{f}_1^* \delta, d \in \mathcal{D}\}$.

In the third step, the third penalty function is optimized over all feasible solutions that are optimal for the second objective among all optimal solutions for the first objective, $d^*_{Lexico} \in \arg\min\{f_3(d): f_1(d) \leq \bar{f}_1^* \delta, f_2(d) \leq \bar{f}_2^* \delta, d \in \mathcal{D}\}$.

The solution $d^*_{Lexico}$ is the final outcome of the Lexico which we used to make FIGS. 7 and 8.

Appendix A.2. 2pεc

The 2pεc approach is a combination of Lexico and goal programming. The underling idea of this approach comes from this observation that Lexico tends to generate extreme solutions mainly because in each step it always searches among optimal solutions of the previous step. However, in practice, that is only necessary if the optimal objective value of the previous step is larger (i.e., worse) than the goal defined for that step. Otherwise, searching among solutions satisfying the goal can be sufficient in practice. With this in mind, 2pεc, as the name suggests, consists of two phases. The first phase is similar to the Lexico with the only difference being in the right-hand-side values of the constraints imposed in each step. Specifically, the following three optimization problems need to be solved:

$$\overline{f_1}^* := \min\{f_1(d) : d \in \mathcal{D}\},$$

$$\overline{f_2}^* := \min\{f_2(d) : f_1(d) \leq \max\{\overline{f_1}^*\delta, g_1\}, d \in \mathcal{D}\},$$

$$\overline{f_3}^* := \min\{f_3(d) : f_1(d) \leq \max\{\overline{f_1}^*\delta, g_1\}, f_2(d) \leq \max\{\overline{f_2}^*\delta, g_2\}, d \in \mathcal{D}\}.$$

The issue about the first phase is that the solution corresponding to $f_3^*$ may not be Pareto-optimal if $\max\{\overline{f_1}^*\delta, g_1\} \neq \overline{f_1}^*$ or $\max\{\overline{f_2}^*\delta, g_2\} \neq \overline{f_2}^*$. So, the second step is designed to ensure that a Pareto-optimal solution will be generated. Similar to the first phase, the second phase will also have three steps and in each step one optimization problem needs to be solved. The optimization problems are as follows:

$$\overline{f_1}^* : \min\{f_1(d) : f_2(d) \leq \max\{\overline{f_2}^*\delta, g_2\}, _3(d) \leq \max\{\overline{f_3}^*\delta, g_3\}, d \in \mathcal{D}\},$$

$$\overline{f_2}^* : \min\{f_2(d) : f_1(d) \leq \overline{f_1}^*\delta, f_3(d) \leq \max\{\overline{f_3}^*\delta, g_3\}, d \in \mathcal{D}\},$$

$$d_{*2p \in c} \in \arg\min\{f_3(d) : f_1(d) \leq \overline{f_1}^*\delta, f_2(d) \leq \overline{f_2}^*\delta, d \in \mathcal{D}\}.$$

The solution $d_{*2p \in c}$ is the final outcome of 2pεc which we used it to make FIGS. 7 and 8. Some steps of the second phase may be redundant and therefore can be skipped. For example, if $\max\{\overline{f_1}^*\delta, g_1\} = \overline{f_1}^*$ and $\max\{\overline{f_2}^*\delta, g_2\} = \overline{f_2}^*$ then the solution corresponding to $\overline{f_3}^*$ is Pareto-optimal and can be named as $d_{*2p \in c}$. So, in that case there is no need to call the second phase at all. If $\max\{\overline{f_2}^*\delta, g_2\} = \overline{f_2}^*$ and $\max\{\overline{f_3}^*\delta, g_3\} = \overline{f_3}^*$ then the solution corresponding to $\overline{f_1}^*$ is Pareto-optimal and can be named as $d_{*2p \in c}$. So, in that case there is no need to call steps 2 and 3 of the second phase at all. Finally, if $\max\{\overline{f_3}^*\delta, g_3\} = \overline{f_3}^*$ then the solution corresponding to $\overline{f_2}^*$ is Pareto-optimal and can be named as $d_{*2p \in c}$. So, in that case there is no need to call step 3 of the second phase at all.

Example Implementations—Methods and Systems

The techniques and algorithms described above may be implemented via a number of practical embodiments, whether through systems (hardware) or computer-implemented methods or services. Some example embodiments will now be described, however it is to be understood that these examples are not necessarily limiting of the scope of claims hereof.

Figure 9:
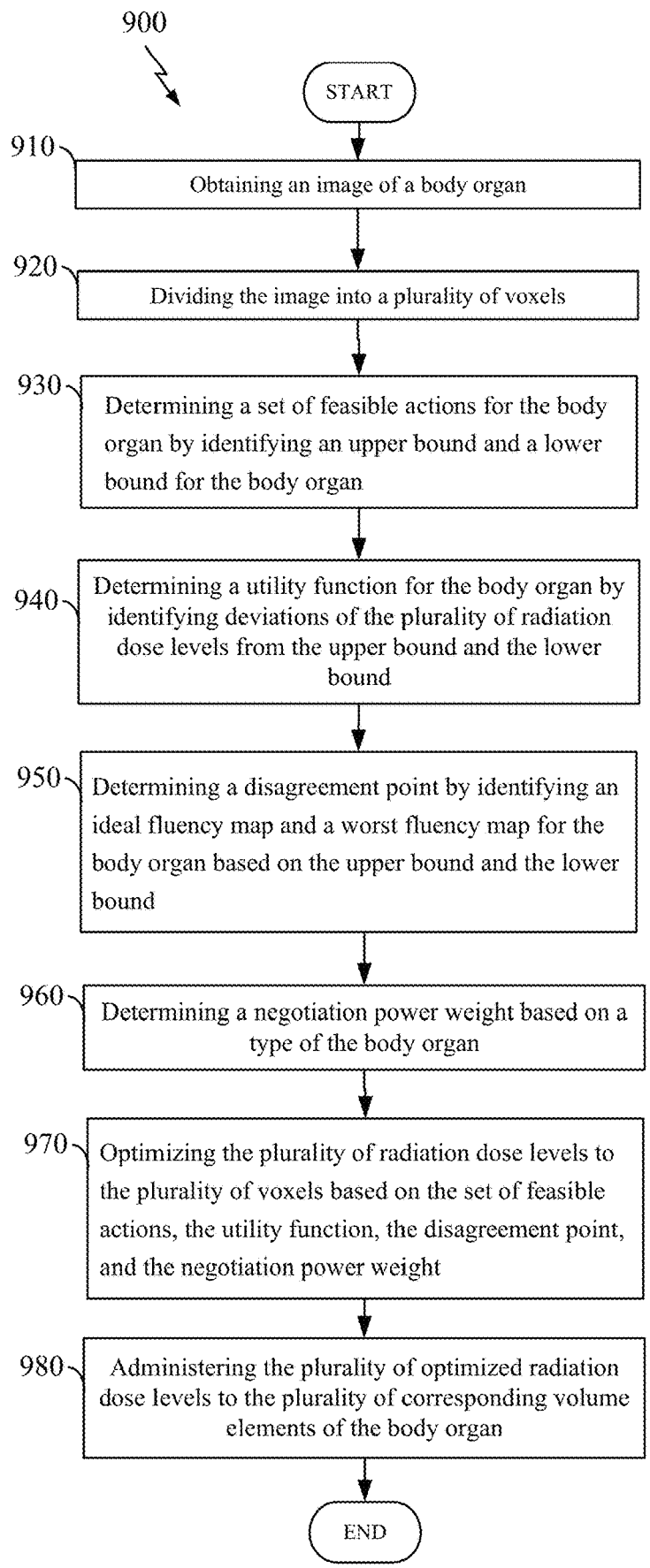
FIG. 9 is a flow chart illustrating an exemplary process for motion taxonomy for manipulation embedding according to some aspects of the disclosure.

Referring now to FIG. 9, an example of a method for generating an optimized IMRT treatment regimen is shown. FIG. 9 is a flow chart illustrating an exemplary process for fluency map optimization using a cooperative game solution approach in accordance with some aspects of the present disclosure. As described below, a particular implementation may omit some or all illustrated features and may not require some illustrated features to implement all embodiments. In some examples, any suitable apparatus or means for carrying out the functions or algorithm described below may carry out the process 900.

In block 910, an apparatus may obtain an image of a body organ. For example, the image may include a three-dimensional computed tomography (CT) image, or another type of image modality. A processor of a computer, or a processor of a treatment apparatus, may obtain the image from an external source, such as a data repository or patient electronic medical record. In some examples, the image may include an image of multiple body organs. In further examples, the image may include multiple images of a body organ or multiple body organs to show a 3D shape of the body organ or multiple body organs. In some examples, the apparatus may receive the image of the body organ or access the memory, which contains the image of the body organ.

In block 920, the apparatus may divide the image into multiple voxels corresponding to multiple volume elements of the body organ. That is, the organ may be considered as an arrangement of small volume elements that corresponds to multiple voxels of the 3D image of the organ. Thus, a small volume element of the body organ can be represented as a voxel in the 3D image of the body organ. In some examples, the image of the body organ includes an image of multiple body organs. Then, the apparatus may divide the image by categorizing the multiple voxels based on the multiple body organs.

In block 930, the apparatus may determine a set of feasible actions for the body organ by identifying an upper bound and a lower bound for the body organ. The set of feasible action may be determined by identifying an upper bound and a lower bound for the body organ. The upper bound may be equal to a maximum radiation dose level among multiple radiation dose levels delivered to the multiple corresponding voxels. The lower bound may be equal to a minimum radiation dose level among the multiple radiation dose levels. The set of feasible actions for the body organ may be defined as $X := d: d \in D, l'_s \leq d_v \leq u_s, \forall v \in V_s$ and $\forall s \in S$, where $l' := (l'_1, \ldots, l'_{|S|})$ and $u' := (u'_1, \ldots, u'_{|S|})$ are the vectors of bounds, $l'_S$ and $u'_S$ represent the lower and upper bound for organ $s \in S$, respectively. Here, the set of feasible actions is X and is the set of all possible fluency maps (i.e., D) with some additional constraints on radiation doses delivered to each voxel within the body organ. In some examples, if the initially prescribed dose levels are feasible, $l'_S$ and $u'_S$ can be equated with $l_S$ and $u_S$ (the lower and upper dose level prescribed for the body organ s), respectively.

In block 940, the apparatus may determine a utility function for the body organ by identifying deviations of the plurality of radiation dose levels from the upper bound and the lower bound. In some examples, the utility function is a quadratic penalty function. However, it should be appreciated that the utility function can be any form of penalty functions. In further examples, the utility function may be determined based on a difference between the plurality of radiation dose levels and the upper bound, a difference between the plurality of radiation dose levels and the lower bound. For example, the utility function can be expressed as: $\Sigma_{v \in V} \alpha_v [(d_v - u)_+^2 + (l - d_v)_+^2]$, where v is the voxel of the plurality of voxels, V is a set of all voxels in the image, $\alpha_v$ is a voxel weight of the voxel v, $d_v$ is the radiation dose level for the voxel v, and u is the lower bound, and l is the upper bound. In some instances, the utility function is further determined based on an organ weight. The organ weight can be determined based on a size of the body organ.

In block 950, the apparatus may determine a disagreement point by identifying an ideal fluency map and a worst fluency map for the body organ based on the upper bound and the lower bound. The ideal fluency map can minimize the deviations of the plurality of radiation dose levels from the upper bound and the lower bound. The ideal fluency map may be similar to the quadratic fluency map optimization. For example, the ideal fluency map may be expressed as: $m_s = u_s(d) = f_s(d) = \Sigma_{v \in V} \alpha_v[(d_v-u)_+^2 + (l-d_v)_+^2]$, where $m_s$ is the ideal fluency map for the organ s, v is the voxel of the plurality of voxels, V is a set of all voxels in the image, $\alpha_v$ is a voxel weight of the voxel v, $d_v$ is the radiation dose level for the voxel v, u is the lower bound, and l is the upper bound.

The worst (ie, least optimal) fluency map for the body organ may maximize the deviations of the plurality of radiation dose levels from the upper bound and the lower bound. The worst fluency map can be obtained based on the sum of all other organs' utility functions to be minimized on the set of feasible actions with some constraints. For example, $r_s = u_s(d')$, where $$d'^s \in \mathrm{argmax}_{s' \in S} u_s\left(d''^{s'}\right),$$

$$d''^{s'} \in \mathrm{argmin}_{d \in X} \sum_{k' \in S} u_{s'}(d) : d_v^s - \epsilon \leq d_v \leq d_v^s + \epsilon, \forall v \in V_s.$$

In some examples, the apparatus may also set a constraint such the multiple radiation dose levels are between the upper bound and the lower bound. For example, the constraint can be expressed as: $\Sigma_{v \in V} a_v[(d_v-u')_+^2 + (l'-d_v)_+^2] = 0$, v is the voxel of the plurality of voxels, V is a set of all voxels in the image, $a_v$ is a voxel weight of the voxel v, $d_v$ is the radiation dose level for the voxel v, u' is the lower bound, and l' is the upper bound.

In block 960, the apparatus may determine a negotiation power weight based on a type of the body organ such that the negotiation power weight is higher when the body organ includes the cancerous tissue than when the body organ is devoid of the cancerous tissue. The negotiation power weight is different from an organ weight. For example, the organ weight emphasizes the importance of different organs in finding the feasible dose levels, where a higher weight results in a tighter dose level. However, the negotiating power weight may emphasize the power of organ in the bargaining process, where a higher power results in a final solution more preferable for the body organ.

In block 970, the apparatus may optimize the plurality of radiation dose levels to the plurality of voxels based on the set of feasible actions, the utility function, the disagreement point, and the negotiation power weight. In some examples, the optimizing the multiple radiation dose levels can include optimizing an area between the ideal fluency map and the worst fluency map based on a Nash Social Welfare. The optimizing the multiple radiation dose levels includes optimizing a fluency map bargaining game. The fluency map bargaining game can be expressed as:

$$\mathrm{max}\Pi_{s \in S}\left[\frac{r_s - u_s(d)}{r_s - m_s}\right]^{p_s},$$

such that $d_v = \Sigma_{n \in N} D_{vn} x_n$ and $x_n \geq 0$, where $r_s$ is the worst dose level, $m_s$ is the ideal dose level, $u_s(d)$ is the penalty function, d is the plurality of radiation dose levels, s is the body organ, S is a plurality of body organs including the body organ, and $p_s$ is the negotiation power weight for the body organ s.

In block 980, the apparatus may administer the multiple optimized radiation dose levels to the plurality of corresponding volume elements of the body organ.

Hardware Configuration Example

Figure 10:
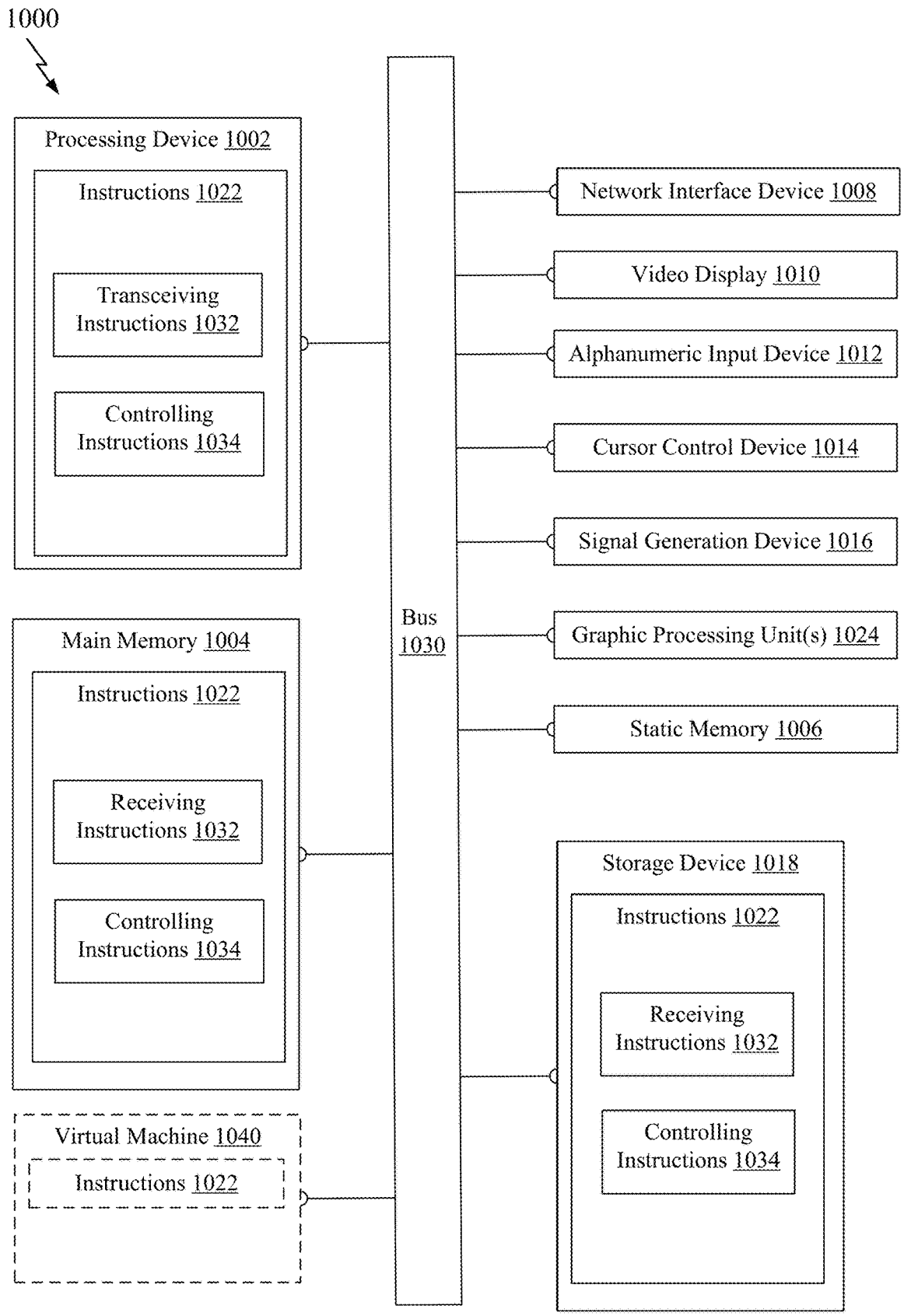
FIG. 10 is a block diagram conceptually illustrating an example of a hardware implementation for the methods disclosed herein.

FIG. 10 is a block diagram conceptually illustrating an example apparatus of a computer system 1000 within which a set of instructions, for causing the apparatus to perform any one or more of the methods disclosed herein, may be executed. In alternative implementations, the apparatus may be connected (such as networked) to other apparatus in a LAN, an intranet, an extranet, and/or the Internet.

The apparatus may operate in the capacity of a server or a client machine in a client-server network environment, as a peer machine in a peer-to-peer (or distributed) network environment, or as a server or a client machine in a cloud computing infrastructure or environment. The apparatus may be a server computer, a personal computer (PC), a tablet PC, a set-top box (STB), a Personal Digital Assistant (PDA), a cellular telephone, a web appliance, a server, a network router, a switch or bridge, or any apparatus capable of executing a set of instructions (sequential or otherwise) that specify actions to be taken by that apparatus. Further, while a single apparatus is illustrated, the term "apparatus" shall also be taken to include any collection of apparatuses that individually or jointly execute a set (or multiple sets) of instructions to perform any one or more of the methods discussed herein.

The example computer system 1000 includes a processing device 1002, a main memory 1004 (such as read-only memory (ROM), flash memory, dynamic random access memory (DRAM) such as synchronous DRAM (SDRAM) or DRAM, etc.), a static memory 1006 (such as flash memory, static random access memory (SRAM), etc.), and a data storage device 1018, which communicate with each other via a bus 1030.

Processing device 1002 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 1002 may also be one or more special-purpose processing devices such as an application specific integrated circuit (ASIC), a field programmable gate array (FPGA), a digital signal processor (DSP), network processor, or the like. In some embodiments, the processing device 1002 may be integrated into an IMRT therapeutic device. The processing device 2302 is configured to execute instructions 1022 for performing the operations and steps discussed herein.

The computer system 1000 may further include a network interface device 1008 for connecting to the LAN, intranet, internet, and/or the extranet. The computer system 1000 also may include a video display unit 1010 (such as a liquid crystal display (LCD) or a cathode ray tube (CRT)), an alphanumeric input device 1012 (such as a keyboard), a cursor control device 1014 (such as a mouse), a signal generation device 1016 (such as a speaker), and a graphic processing unit 1024 (such as a graphics card).

The data storage device 1018 may be a machine-readable storage medium 1028 (also known as a computer-readable medium) on which is stored one or more sets of instructions or software 1022 embodying any one or more of the methods or functions described herein. The instructions 1022 may also reside, completely or at least partially, within the main memory 1004 and/or within the processing device 1002 during execution thereof by the computer system 1000, the main memory 1004 and the processing device 1002 also constituting machine-readable storage media.

In one implementation, the instructions 1022 include transceiving instructions for obtaining an image of a body organ from a three-dimensional computed tomography (CT) scanner; and administering multiple optimized radiation dose levels to a body organ at blocks 910 and 980 of FIG. 9. The instructions 1022 may further include controlling instructions 1034 for determining a set of feasible actions for the body organ by identifying an upper bound and a lower bound for the body organ, determining a utility function for the body organ by identifying deviations of the plurality of radiation dose levels from the upper bound and the lower bound, determining a disagreement point by identifying an ideal fluency map and a worst fluency map for the body organ based on the upper bound and the lower bound, determining a negotiation power weight based on a type of the body organ, and/or optimizing the plurality of radiation dose levels to the plurality of voxels based on the set of feasible actions, the utility function at blocks 920, 930, 940, 950, 960, and/or 970 of FIG. 9. Furthermore, the instructions 1022 may be utilized to either send a fluency map to a therapy-delivering device (or a network on which a therapy-delivering device exists), or may be stored on a memory that is part of the therapy-delivery device itself. While the machine-readable storage medium 1018 is shown in an example implementation to be a single medium, the term "machine-readable storage medium" should be taken to include a single medium or multiple media (such as a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media. The term "machine-readable storage medium" shall accordingly exclude transitory storage mediums such as signals unless otherwise specified by identifying the machine-readable storage medium as a transitory storage medium or transitory machine-readable storage medium.

In another implementation, a virtual machine 1040 may include a module for executing instructions such as receiving instructions 1032, generating instructions 1034, and/or modifying instructions 1036. In computing, a virtual machine (VM) is an emulation of a computer system. Virtual machines are based on computer architectures and provide functionality of a physical computer. Their implementations may involve specialized hardware, software, or a combination of hardware and software.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "modifying" or "providing" or "calculating" or "determining" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices. The present disclosure also relates to an apparatus for performing the operations herein. This apparatus may be specially constructed for the intended purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The algorithms and displays presented herein are not inherently related to any particular computer or other apparatus. Various general purpose systems may be used with programs in accordance with the teachings herein, or it may prove convenient to construct a more specialized apparatus to perform the method. The structure for a variety of these systems will appear as set forth in the description below. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (such as a computer). For example, a machine-readable (such as computer-readable) medium includes a machine (such as a computer) readable storage medium such as a read only memory ("ROM"), random access memory ("RAM"), magnetic disk storage media, optical storage media, flash memory devices, etc.

In the foregoing specification, implementations of the disclosure have been described with reference to specific example implementations thereof. It will be evident that various modifications may be made thereto without departing from the broader spirit and scope of implementations of the disclosure as set forth in the following claims. The specification and drawings are, accordingly, to be regarded in an illustrative sense rather than a restrictive sense.

What is claimed is:

1. A method for controlled tumoricidal radiation dose delivery, comprising:
   obtaining an image of a body organ;
   dividing the image into a plurality of voxels corresponding to a plurality of volume elements of the body organ;
   determining a set of feasible actions for the body organ by identifying an upper bound and a lower bound for the body organ, wherein the upper bound is equal to a maximum radiation dose level among a plurality of radiation dose levels delivered to the plurality of corresponding voxels, wherein the lower bound is equal to a minimum radiation dose level among the plurality of radiation dose levels;
   determining a utility function for the body organ by identifying deviations of the plurality of radiation dose levels from the upper bound and the lower bound;
   determining a disagreement point by identifying an ideal fluency map and a worst fluency map for the body organ based on the upper bound and the lower bound, wherein the ideal fluency map minimizes the deviations of the plurality of radiation dose levels from the upper bound and the lower bound, wherein the worst fluency map for the body organ maximizes the deviations of the plurality of radiation dose levels from the upper bound and the lower bound,
   determining a negotiation power weight based on a type of the body organ such that the negotiation power weight is higher when the body organ includes a cancerous tissue than when the body organ is devoid of the cancerous tissue; and
   optimizing the plurality of radiation dose levels to the plurality of voxels based on the set of feasible actions, the utility function, the disagreement point, and the negotiation power weight.

2. The method of claim 1, further comprising determining an organ weight based on a size of the body organ.

3. The method of claim 1, wherein the image is a three-dimensional computed tomography (CT) image.

4. The method of claim 1, wherein the image of the body organ comprises an image of a plurality of body organs, and
   wherein the dividing the image comprises categorizing the plurality of voxels based on the plurality of body organs.

5. The method of claim 1, wherein the utility function is a quadratic penalty function.

6. The method of claim 1, wherein the utility function is determined based on a difference between the plurality of radiation dose levels and the upper bound, a difference between the plurality of radiation dose levels and the lower bound.

7. The method of claim 1, wherein the utility function is: $\Sigma_{v \in V} a_v [(d_v-u)_+^2 + (l-d_v)_+^2]$, where v is the voxel of the plurality of voxels, V is a set of all voxels in the image, $a_v$ is a voxel weight of the voxel v, $d_v$ is the radiation dose level for the voxel v, and u is the lower bound, and l is the upper bound.

8. The method of claim 1, wherein the utility function is further determined based on an organ weight.

9. The method of claim 1, further comprising:
   setting a constraint such that the plurality of radiation dose levels are between the upper bound and the lower bound.

10. The method of claim 9, wherein the constraint is: $\Sigma_{v \in V} a_v [(d_v-u')_+^2 + (l'-d_v)_+^2] = 0$, v is the voxel of the plurality of voxels, V is a set of all voxels in the image, $a_v$ is a voxel weight of the voxel v, $d_v$ is the radiation dose level for the voxel v, u' is the lower bound, and l' is the upper bound.

11. The method of claim 1, wherein the optimizing the plurality of radiation dose levels comprises optimizing an area between the ideal fluency map and the worst fluency map based on a Nash Social Welfare.

12. The method of claim 1, wherein the optimizing the plurality of radiation dose levels comprises optimizing a fluency map bargaining game,
   wherein the fluency map bargaining game is:

$$\max \Pi_{s \in S} \left[ \frac{r_s - u_s(d)}{r_s - m_s} \right]^{p_s},$$

such that $d_v = \Sigma_{n \in N} D_{vn} x_n$ and $x_n \geq 0$, where $r_s$ is the worst dose level, $m_s$ is the ideal dose level, $u_s(d)$ is the penalty function, d is the plurality of radiation dose levels, s is the body organ, S is a plurality of body organs including the body organ, and $p_s$ is the negotiation power weight for the body organ s.

13. The method of claim 1, further comprising:
   administering the plurality of optimized radiation dose levels to the plurality of corresponding volume elements of the body organ.

14. An apparatus for controlled tumoricidal radiation dose delivery, comprising:
   a memory; and
   a processor coupled with the memory and configured to:
      obtain an image of a body organ;
      divide the image into a plurality of voxels corresponding to a plurality of volume elements of the body organ;
      determine a set of feasible actions for the body organ by identifying an upper bound and a lower bound for the body organ, wherein the upper bound is equal to a maximum radiation dose level among a plurality of radiation dose levels delivered to the plurality of corresponding voxels, wherein the lower bound is equal to a minimum radiation dose level among the plurality of radiation dose levels;
      determine a utility function for the body organ by identifying deviations of the plurality of radiation dose levels from the upper bound and the lower bound;
      determine a disagreement point by identifying an ideal fluency map and a worst fluency map for the body organ based on the upper bound and the lower bound, wherein the ideal fluency map minimizes the deviations of the plurality of radiation dose levels from the upper bound and the lower bound, wherein the worst fluency map for the body organ maximizes the deviations of the plurality of radiation dose levels from the upper bound and the lower bound,
      determine a negotiation power weight based on a type of the body organ such that the negotiation power weight is higher when the body organ includes a cancerous tissue than when the body organ is devoid of the cancerous tissue; and
      optimize the plurality of radiation dose levels to the plurality of voxels based on the set of feasible actions, the utility function, the disagreement point, and the negotiation power weight.

15. The apparatus of claim 14, wherein the processor coupled with the memory is further configured to:
determine an organ weight based on a size of the body organ.

16. The apparatus of claim 14, wherein the image is a three-dimensional computed tomography (CT) image.

17. The apparatus of claim 14, wherein the image of the body organ comprises an image of a plurality of body organs, and
wherein the dividing the image comprises categorizing the plurality of voxels based on the plurality of body organs.

18. The apparatus of claim 14, wherein the utility function is a quadratic penalty function.

19. The method of claim 14, wherein the utility function is determined based on a difference between the plurality of radiation dose levels and the upper bound, a difference between the plurality of radiation dose levels and the lower bound.

20. The apparatus of claim 14, wherein the utility function is:
$\Sigma_{v \in V} a_v [(d_v-u)_+^2 + (l-d_v)_+^2]$, where v is the voxel of the plurality of voxels, V is a set of all voxels in the image, $a_v$ is a voxel weight of the voxel v, $d_v$ is the radiation dose level for the voxel v, and u is the lower bound, and l is the upper bound.

21. The apparatus of claim 14, wherein the utility function is further determined based on an organ weight.

22. The apparatus of claim 14, wherein the processor coupled with the memory is further configured to:
set a constraint such that the plurality of radiation dose levels are between the upper bound and the lower bound.

23. The apparatus of claim 22, wherein the constraint is:
$\Sigma_{v \in V} a_v [(d_v-u')_+^2 + (l'-d_v)_+^2] = 0$, v is the voxel of the plurality of voxels, V is a set of all voxels in the image, $a_v$ is a voxel weight of the voxel v, $d_v$ is the radiation dose level for the voxel v, u' is the lower bound, and l' is the upper bound.

24. The apparatus of claim 14, wherein the optimizing the plurality of radiation dose levels comprises optimizing an area between the ideal fluency map and the worst fluency map based on a Nash Social Welfare.

25. The apparatus of claim 14, wherein the optimizing the plurality of radiation dose levels comprises optimizing a fluency map bargaining game,
wherein the fluency map bargaining game is:

$$\max \Pi_{s \in S} \left[ \frac{r_s - u_s(d)}{r_s - m_s} \right]^{p_s},$$

such that $d_v = \Sigma_{n \in N} D_{vn} x_n$ and $x_n \geq 0$, where $r_s$ is the worst dose level, $m_s$ is the ideal dose level, $u_s(d)$ is the penalty function, d is the plurality of radiation dose levels, s is the body organ, S is a plurality of body organs including the body organ, and $p_s$ is the negotiation power weight for the body organ s.

26. The apparatus of claim 14, wherein the processor coupled with the memory is further configured to:
administer the plurality of optimized radiation dose levels to the plurality of corresponding volume elements of the body organ.

* * * * *